United States Patent [19]
Collins et al.

[11] Patent Number: 5,024,944
[45] Date of Patent: Jun. 18, 1991

[54] TRANSFORMATION, SOMATIC EMBRYOGENESIS AND WHOLE PLANT REGENERATION METHOD FOR GLYCINE SPECIES

[75] Inventors: Glenn B. Collins; David F. Hildebrand; Paul A. Lazzeri, all of Lexington, Ky.; Thomas R. Adams, North Stonington, Conn.; Wayne A. Parrott, Versailles; Lynn M. Hartweck, Lexington, both of Ky.

[73] Assignees: Lubrizol Genetics, Inc., Wickliffe, Ohio; The University of Kentucky Research Foundation, Inc., Lexington, Ky.

[21] Appl. No.: 63,342

[22] Filed: Jun. 15, 1987

Related U.S. Application Data

[63] Continuation-in-part of Ser. No. 893,256, Aug. 4, 1986, abandoned.

[51] Int. Cl.$^5$ .......................... C12N 15/00; C12N 5/00
[52] U.S. Cl. ............................ 435/172.3; 435/240.49; 435/240.5; 435/240.54; 935/67
[58] Field of Search ............. 435/172.3, 240.49, 240.5, 435/240.54

[56] References Cited

U.S. PATENT DOCUMENTS 4,684,612  8/1987  Hemphill .

OTHER PUBLICATIONS

Barwale et al., 1986, Planta 167:473–481.
Kameya et al., 1981, Plant Sci. Lett. 21:289–294.
Sengupta-Gopalan et al., 1985, Proc. Natl. Acad. Sci., U.S.A., 82:3320–3324.
De Block et al., 1984, EMBO J, 3(8):1681–1689.
Owens et al., 1985, Plant Physiol., 77:87–94.
Lippmann et al., 1984, Plant Cell Rep., 3:215–218.
Ranch et al., 1985, In Vitro, 21(11):653–658.
Raquin, C., 1983, Z. Pflanzenphysiol., 111:453–457.
Lazzeri et al., 1985, Plant Mol. Biol. Rep., 3(4):160–167.
Barwale, U. B. (1985), "Screening of soybean cultivars for plant regeneration of soybean plants from undifferentiated tissue," Master's Thesis, cataloged by the University of Illinois Library, Mar. 16, 1986, p. 59.
Hood, E. E. et al. (1984), Bio/Technology, 2:702–709.
Hood (1986), J. Bact., 168:1283–1290.
Wyndaele, R. et al. (1985), Plant Cell Physiol., 26:1147–1154.
Bialy, H. (1985), Bio/Technology, 3:200–201.
Kudirka, D. T. et al. (1986), Can. J. Genet. Cytol., 28:808–817.
Simpson, R. B. et al. (1986), Plant Mol. Biol., 6:403–415.
Byrne, M. C. et al. (1987), Plant Cell. Tissue and Organ Culture, 8:3–15.
Shahin, E. A. and Simpson, R. B. (1986), Abstract for presentation at the Conference on Molecular and Cellular Biology of the Soybean, Ames, Iowa.
Williams, E. G. and Maheswaran, G. (1986), Annals of Bot., 57:443–462.

*Primary Examiner*—Elizabeth C. Weimar
*Assistant Examiner*—David T. Fox
*Attorney, Agent, or Firm*—Greenlee and Associates

[57] ABSTRACT

A method for somatic embryogenesis of soybean, (*Glycine max*), *Glycine soja* and other Glycine species is provided using immature cotyledon tissue, preferably with the embryonic axis removed, comprising culturing said tissue on a medium containing auxin, preferably NAA at a concentration of at least about 15 mg/l. A further method for such somatic embryogenesis is provided wherein the culture medium contains a synergistically acting lowered carbohydrate and auxin concentration. Particularly embryogenic cells of such tissue are identified and improved maceration methods for contacting such cells with regeneration and transformation media are disclosed.

Methods for transforming somatic tissue from soybean and other Glycine species are also provided.

Whole, fertile, transformed plants are obtained.

31 Claims, 1 Drawing Sheet

TRANSFORMATION, SOMATIC EMBRYOGENESIS AND WHOLE PLANT REGENERATION METHOD FOR GLYCINE SPECIES

CROSS REFERENCE TO RELATED APPLICATION

This application is a continuation-in-part application of U.S. Ser. No. 893,256, filed Aug. 4, 1986, now abandoned.

FIELD OF THE INVENTION

This invention relates to methods of transforming and regenerating whole plants from somatic tissue of soybean and other Glycine species.

BACKGROUND OF THE INVENTION

A method for achieving regeneration of soybean and its relatives from somatic tissue cultures has long been sought. Unlike such easily regenerable species as tobacco and petunia, soybean has resisted prior attempts to regenerate whole plants from somatic tissues. Such methods are very desirable in allowing the induction of desirable traits into soybean or species capable of breeding therewith (such as *G. soja*) via somaclonal variation. Such methods would also be of benefit to genetic engineers in allowing transformation of cells by infection with Agrobacteria or by other means resulting in transformed cells in culture containing foreign (heterologous) DNA which could then be regenerated into whole plants bearing seed and expressing foreign genes.

Few methods for regenerating Glycine subgenus soja (comprising *G. max* (soybean) and *G. soja*) have been developed, although greater success has been achieved with wild relatives such as *G. canescens* and *G. clandestina*. See P. A. Lazzeri, et al. (1985) "A Procedure for Plant Regeneration from Immature Cotyledon Tissue of Soybean," Plant Molecular Biology Reporter Vol. 3, No. 4, 160-167, and D. F. Hildebrand, et al. (1986) "Soybean [*Glycine max* (L.) Merr.]," Biotechnology in Agriculture and Forestry Vol. 2: Crops I (Y. P. S. Bajaj, ed.) 283-308.

Most manipulations of Glycine species described in the literature involving embryogenesis provide a basal medium containing an auxin as an induction medium for the development of embryoids. After embryo formation, the embryos may be moved to a maturation medium and then to a medium containing cytokinin and reduced auxin for shooting. However the desirability of using NAA in high concentrations or synergistically lowered concentrations of carbohydrates and auxins has not previously been recognized as an aid in attaining high frequencies of normal somatic embryos. Further, specific cotyledonary cells giving rise to somatic embryos in media containing any auxin have not been identified and isolated so as to provide high efficiency in a regeneration method of *G. max* or other Glycine species.

W. D. Beversdorf, et al., in "Degrees of Differentiation Obtained in Tissue Cultures of Glycine Species," (1977) Crop Sci. Vol. 17, 307-311, first reported somatic embryogenesis, but none of the embryos "germinated." Using an induction medium containing 2,4-D (2,4-dichlorophenoxyacetic acid) and/or NAA (alpha-naphthaleneacetic acid) and 2% sucrose to culture hypocotyl or mature cotyledon tissues or apices, or embryos, of G. max and several related species, Beversdorf, et al. achieved embryo-like structures on some cultivars, but no further development into plantlets. Cotyledon tissues from developing embryos of 56 soybean cultivars developed calli and "non-callus" structures on a medium containing 2 mg/l 2,4-D and 2 mg/l NAA. None of these developed further however.

T. Y. Cheng, et al. (1980), "Plant Regeneration from Soybean Cotyledonary Node Segments in Culture," Plant Sci. Lett. Vol. 19, 91-99, report the stimulation of multiple shoot-bud formation of soybeans in culture using conditioned cotyledonary node segments. The medium used contained 3% sucrose and 0.25 $\mu$M of the auxin IBA (indole butyric acid). This method did not involve the use of somatic tissues, but rather used explants consisting of totipotent cells to evaluate the effectiveness of various media. It is not clearly reported that whole plants capable of independent growth in soil were regenerated.

H. Saka, et al. (1980), "Stimulation of Multiple Shoot Formation on Soybean Stem Nodes in Culture," Plant Sci. Lett Vol. 19, 193-201, similarly describe the formation of shoot-buds on stem nodes or apices of *G. max* using a culture medium containing the auxin IBA and 3% sucrose or other carbohydrate. This work did not involve the use of somatic tissues, but rather used tissues normally competent to produce shoots to evaluate the effectiveness of various media for producing growth. Whole plant regeneration was not reported.

T. Kameya, et al. (1981), "Plant Regeneration from Hypocotyl Sections of Glycine Species," Plant Sci. Lett., Vol. 21 289-294, disclose the use of hypocotyl sections of *G. canescens* and *G. tomentella* cultured on MS medium supplemented with NAA and BA (6-benzylamino purine) at various concentrations to regenerate normal plants. From the eight species tested including *G. max* and *G. soja* regeneration of shoots at high frequency was observed only from hypocotyl sections of *G. canescens* using 1-5 mg/l BA and 0.1 to 2 mg/l NAA. Whole plants were regenerated.

G. C. Phillips, et al. (1981), "Induction and development of somatic embryos from cell suspension cultures of soybean," Plant Cell Tissue Organ Culture, Vol. 1, 123-129 reported obtaining a single shoot from an embryogenic *G. soja* suspension culture. Various auxins were evaluated in combination with basal L2 and SL2 media, including NAA at 0.1 to 13.4 $\mu$M (approximately 0.02 to 2.7 mg/l). Sucrose concentrations from 2.5% to 12.5% were used. The single shoot obtained came from a *G. soja* culture grown on an SL2 medium containing 2.25 $\mu$M 2,4-D (0.45 mg/l), and transferred to an L2 medium containing the same amount of 2,4-D, plus cytokinin, antiauxin and gibberellin biosynthesis inhibitor.

K. K. Kartha, et al. (1981) "Plant Regeneration from meristems of grain legumes: soybean, cowpea, peanut, chickpea and bean," Can. J. Bot. Vol. 59, 1671-1679, describe plant regeneration from shoot apical meristems of soybean on a medium containing 3% sucrose and 1 $\mu$M/l NAA. Whole plants were regenerated; however, this article does not disclose the use of somatic tissue to give rise to new plants, but rather the normal continued differentiation of meristem tissue. The reference is primarily concerned with the determination of optimal growth media for this purpose.

B. D. Reynolds, et al. in an abstract for a presentation at the 79th Annual Meeting of the American Society for Horticultural Science in Ames, Iowa August 8-13, 1982, entitled "Production of Embryoids from Primary and Callus Explants of Soybean," reported production of embryoids from primary explants (hypocotyl, leaf, and root) of *Glycine max* when cultured on various media. This abstract does not define the media clearly nor provide enabling details. No claim to plant regeneration beyond the embryoid stage is made.

M. L. Christianson, et al. (1983), "A Morphogenetically Competent Soybean Suspension Culture Vol. 222, 632-634, report the regeneration of plantlets from pieces of the embryonic axis of *G. max* using as an embryo induction medium MS (Murashige and Skoog) medium with the nitrogen salts therein replaced by 20 $\mu$M ammonium citrate and also containing 5 mg/l 2,4-D or IAA (indole-3-acetic acid). This reference discloses that the nitrogen substitution was critical to the method. Only one exceptional piece of tissue formed embryos. This, therefore, may have been an accidental and non-reproducible event, and in fact the literature does not report this work having been successfully repeated. Transfer of the embryoids to a medium containing 0.005 mg/l IBA and 0.2 mg/l BA gave rise to shoot formation. Transfer of the shoots to a basal medium containing 0.1 mg/l IAA resulted in root formation to produce plantlets.

U.S. Pat. No. 4,548,901 to Christianson, et al. is based on the above described work and claims an improvement in a method for producing a morphogenetically competent plantlet regeneration culture wherein explants of a large-seeded legume plant are successively cultured and selectively transferred, comprising culturing in a medium containing exogenous auxin and ammonium salt, said medium being free of nitrate ion. This patent also claims a method for generating legume bipolar embryoids which comprises several culturing steps including the use of the medium containing exogenous auxin and an ammonium salt, said medium being free of nitrate ion. The examples of this application are as described in the above article except that the mention of rooting is couched in the present tense, apparently indicating that rooting had not been achieved at the time of filing the patent application.

Neither the Christianson, et al. article nor the Christianson, et al. patent disclose or claim the regeneration of whole plants capable of independent growth in soil, nor capable of seed production.

J. M. Widholm, et al. (1983), "Shoot Regeneration from *Glycine canescens* Tissue Cultures," Plant Cell Reports, Vol. 2, 19-20, report shoot induction from calli obtained from cotyledons and hypocotyls of *G. canescens* using several media including media containing 0.5 mg/l NAA and 3% sucrose. Whole plants were not regenerated, and root formation was infrequent.

O. L. Gamborg, et al. (1983), "Somatic Embryogenesis in Cell Cultures of Glycine Species," Plant Cell Reports, Vol. 2, 209-212, report somatic embryogenesis from cell suspension culture of hypocotyl tissue in several Glycine species including three cultivars (out of seven tested) of *Glycine max*. The embryoid induction medium consisted of the major salts of SL, the micronutrients and vitamins of B5, 10 mg/l casamino acids, 15 $\mu$M adenine sulfate, 0.2 $\mu$M Picloram (0.04 mg/l) and 0.025-00.25 $\mu$M AMO 1618. It was discovered that picloram was most effective for embryoid induction but that it could be replaced by 0.5 to 2.0 $\mu$M 2,4-D (0.1 to 0.4 mg/l). No embryoids were induced when NAA was used as the auxin. After embryoids were induced they were transferred to an SL growth medium containing cytokinins. Roots, but no shoots were formed.

European Patent Application No. 85109344.3 by Sungene Technologies Corp., published Feb. 19, 1986, discloses a process for regenerating soybeans comprising the use of four separate media, an embryoid inducing medium, an embryoid maturation medium, a shooting medium, and a rooting medium. The embryo induction medium is disclosed as containing 0.5 to 10 mg/l 2,4-D or 1.0 to 3.0 mg/l IAA plus 3.0 to 10 mg/l 2,4-D and 2% to 3% sucrose. The examples do not definitely disclose that root formation was attained; the claims are directed to "plantlets."

B. J. Li, et al. (1985), "Somatic embryogenesis and plantlet regeneration in the soybean *Glycine max*", Plant Cell Reports, Vol. 4, 344-347, report that they obtained plantlets from single cells taken from immature soybean embryos. It is disclosed that it is necessary to first freeze the pods in liquid nitrogen then transfer them to a 60 degree C. water bath for 20 minutes. The immature embryos are dissected and cut into small segments for culturing. The filtering techniques used to obtain single cells from the cultures thus produced were reported as 95% effective. The embryo induction medium contained 2% sucrose and 1 to 2 mg/l 2,4-D. The regeneration of plantlets was described, but no regeneration of whole plants was reported. Applicants herein have attempted to repeat this work without success, as the freezing and rewarming of tissue kills it or destroys its ability to grow further.

B. Lippmann, et al. (1984), "Induction of somatic embryos in cotyledonary tissue of soybean, *Glycine max* L. Merr.," Plant Cell Reports, Vol. 3, 215-218, describe the use of immature cotyledons from G. max to form embryos in a medium containing 0.5 to 1 mg/l 2,4-D and .25 to 2% sucrose. A few cases of shoot differentiation and root formation were observed with L2 medium containing 0.5 $\mu$M/l zeatin. No embryo formation was observed when NAA was used as the auxin rather than 2,4-D. No embryos were formed on media containing sucrose above 2% or glucose above 1.5%. No regeneration of whole plants was reported.

J. E. Grant (1984), "Plant regeneration from cotyledonary tissue of *Glycine canescens*, a perennial wild relative of soybean," Plant Cell Tissue Organ Culture, Vol. 3, 169-173, reports that cotyledon tissue from immature embryos of *G. canescens* was induced to form embryos using MS media containing 0.1 $\mu$M NAA (0.02 mg/l) and 3% sucrose. This work purports to describe the first whole plant regeneration from a Glycine species, but does not disclose regeneration of *G. max*.

J. P. Ranch, et al. (1985), "Plant Regeneration from Embryo-Derived Tissue Cultures of Soybeans, In Vitro Cellular & Developmental Biology, Vol. 21, No. 11, 653-658 describe the use of immature *G. max* and *G. soja* embryos and cotyledons dissected therefrom to produce embryos which were regenerated into whole fertile plants. The embryo induction medium used was MS medium containing 22.5 to 45.2 $\mu$M 2,4-D (5.0 to 10.0 mg/l) and 3% sucrose. An embryo maturation medium, B5 plus IBA and ABA, was used prior to transfer to a germination medium. Whole fertile plants were developed. No use of NAA as an induction medium was reported. Applicants do not concede that this publication may be properly applied as prior art against their invention.

C. A. Newell, et al. (1985) "Protoplast culture and plant regeneration in *Glycine canescens*, Plant Cell Tissue Organ Culture, Vol. 4, 145–149 describe the regeneration of whole plants of *G. canescens* from protoplasts taken from hypocotyl tissue. The embryogenesis induction medium contained BA at 0.4 mg/l and NAA at 0.1 and 1.0 mg/l in some experiments reported. The basic medium consisted of R-Medium major salts and CL-Medium osmoticum, and contained 6.84 mg/l sucrose plus 25 mM each of mannitol, sorbitol, xylitol and inositol.

U. B. Barwale, et al. (1986), "Plant regeneration from callus cultures of several soybean genotypes via embryogenesis and organogenesis," Planta, Vol. 167, 473–481, disclose the use of immature soybean embryos to obtain embryos on an MS medium containing 43.0 μM NAA (8.9 mg/l) and 3% sucrose. Intact embryos were used including both cotyledons and embryonic axes. Whole plants were regenerated.

Master's Thesis by Usha B. Barwale, "Screening of Soybean Cultivars for Plant Regeneration Potential & Regeneration of Soybean Plants from Undifferentiated Tissue," catalogued by the University of Illinois Library Mar. 16, 1986, at page 59 and following, discloses the culturing of whole immature embryos to produce embryogenic calli. The media described contained 3% or more carbohydrate and up to 12 mg/l NAA.

H. R. Kerns, et al. (1986), "Correlation of cotyledonary node shoot proliferation and somatic embryoid development in suspension cultures of soybean (*Glycine max* L. Merr.), "Plant Cell Reports, Vol. 5, 140–143 disclose the induction of embryos on tissue derived from hypocotyl and cotyledon tissues from germinated seeds using a suspension medium containing 6% sucrose and 0.4 mg/l 2,4-D. No regeneration of the embryos into whole plants was reported.

Regeneration of transformed Glycine species plants has not been previously reported, however, several articles discuss Agrobacterium-Glycine interactions.

H. C. Pedersen, et al. (1983), "Induction and in vitro culture of Soybean Crown Gall Tumors," Plant Cell Reports, Vol. 2, 201–204, discuss the first successful infection of *G. max* plants with Agrobacteria by enclosing the inoculation site to prevent dehydration. Except for some sporadic emergence of roots from the transformed callus tissue, this article states the transformed tissue did not develop morphological structures, and attempts to induce regeneration with BAP and NAA were unsuccessful.

E. E. Hood et al. (1984) "Restriction Endonuclease Map of pTiBo542, a Potential Ti Plasmid Vector for Genetic Engineering of Plants", Bio/Technology 2:702–709, describe Agrobacterium infection of soybean (cv. Wayne) utilizing strain A281. A later article by E. E. Hood et al. (1986) "T-DNA and Opine Synthetic Loci in Tumors Incited by *Agrobacterium tumefaciens* A281 on Soybean and Alfalfa Plants, J. Bacteriol. 168:1283–1290 discloses that T-DNA in Agrobacterium infected soybean is of a different length than that in alfalfa.

W. Lranzheng, et al. (1984), "Tumor Induction and Gene Transfer in Annual Species of Glycine by *Agrobacterium tumefaciens*, Proceedings of the World Soybean Research Conference II, Ames, Iowa, 1984, 195–198 describe attempts to induce tumors by infection of 984 varieties of *G. max* as well as large numbers of varieties of other Glycine species by inoculation with cultures of fifteen strains of *Agrobacterium tumefaciens*. Out of 3137 plants of *G. max* treated, tumors were induced on only four. No attempts at plant regeneration were made.

R. Wyndale et al. (1985), "Dynamics of Endogenous IAA and Cytokinins During Growth Cycle of Soybean Crown Gall and Untransformed Callus," Plant Cell Physiol. 26:1145–1154, described Agrobacterium infection and tumor formation in soybean and found high levels of cytokinin in gall tissues.

L. D. Owens et al. (1985), "Genotypic Variability of Soybean Response to Agrobacterium Strains Harboring the Ti or Ri Plasmids," Plant Physiol. 77:87–94, describe response of various soybean genotypes to Agrobacterium infection via tumor formation and opine synthesis.

In a non-enabling report by H. Bialy (1985), "Soybean Transformed; New Role for cGMP", Bio/Technology 3:200–201, a description is given of expression in soybean cell culture of a kanamycin resistance gene transferred via a Ti plasmid. No regeneration was reported.

D. T. Kudirka, et al. (1986), "Interactions of *Agrobacterium tumefaciens* with leaf explants in tissue culture," Can. J. Genet. Cytol. 28:808–817, discloses soybean wound tissues remain susceptible to Agrobacterium infection for only four hours after wounding.

R. B. Simpson et al. (1986), "A disarmed binary vector from *Agrobacterium tumefaciens* functions in *Agrobacterium rhizogenes*," Plant Molecular Biology 6:403–415, discloses the use of the vir region from *A. rhizogenes* in *A. tumefaciens* in a binary vector system to transform soybean (with low efficiency of producing transformed hairy roots). E. A. Shahim and R. B. Simpson, Abstract for presentation at 1986 Conference on Molecular & Cellular Biology of the Soybean, held at Ames, Iowa, entitled "Introduction and Expression of Foreign Genes Into Soybean Via Agrobacterium Rhizogenes" summarizes the work disclosed in the article and states that somatic embryos were formed from transformed soybean root. This abstract also speculates that rhizogenes induced hairy roots can regenerate into whole plants but does not indicate that whole plant regeneration had been achieved or enable such regeneration.

L. D. Owens, et al. (1985) "Genotypic Variability of Soybean Response to Agrobacterium Strains Harboring the Ti or Ri Plasmids," Plant Physiol. Vol. 77, 87–94, describe the effect of *G. max* and *G. soja* genotype and maturity on susceptibility to infection by Agrobacterium. No regeneration of plants from infected tissue is described. Infection was achieved by spreading 10 ml of a bacterial suspension containing $5 \times 10^{10}$ cells/ml on wounds between nodes two and three of plants aged two to three weeks old.

D. Facciotti, et al. (1985), "Light-inducible Expression of a Chimeric Gene in Soybean Tissue Transformed with Agrobacterium," Biotechnology, Vol. 3, 241–246, describes transformation of young soybean plants by injection with *Agrobacterium tumefaciens* containing a kanamycin resistance gene linked to the 5' portion of a soybean small subunit carboxylase gene. Expression of the kanamycin resistance gene in transformed tumorous callus tissue was obtained. No regeneration of transformed tissue was reported.

M. C. Byrne et al. (1987), "Strain and Cultivar Specificity in the Agrobacterium-Soybean Interaction," Plant Cell, Tissue and Organ Cultures 8:3–15, discusses the responses of various soybean genotype to various Agrobacterium strains in terms of tumor formation and describes the expression of kanamycin resistance in transformed tumor tissue.

None of the foregoing art describes somatic embryogenesis and regeneration of whole soybean plants using NAA, or of any Glycine species using auxins at concentrations as high as 15 mg/l or synergistic combinations of carbohydrates at less than 2% and auxins at low percents. Further, none of the art discloses regeneration of a whole transformed plant. Additionally there is no suggestion or disclosure in the art that regeneration efficiencies high enough for effective transformation can be achieved through contacting selected, particularly embryogenic, cells with the DNA to be transferred, nor that such transformation might be accomplished without the use of a selectable marker such as an antibiotic resistance gene.

SUMMARY OF THE INVENTION

Figure 1:
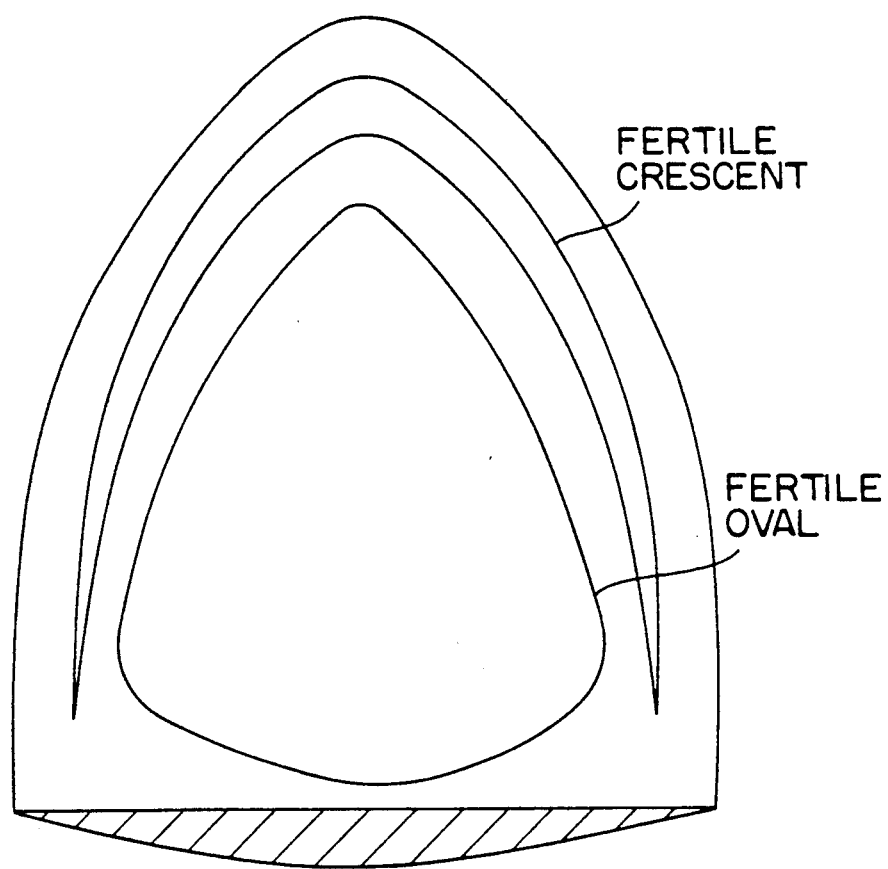
FIG. 1 is a diagram of a soybean cotyledon from an immature embryo showing the "fertile crescent" and "fertile oval" regions of cells most often giving rise to somatic embryos. The cotyledon as shown refers in size lengthwise from 2–4 mm.

A method for producing embryos from somatic tissues is provided comprising excising cotyledon tissue from immature embryos of Glycine species preferably with embryonic axes removed therefrom. Preferably, the Glycine species used is soybean (*Glycine max*) or *Glycine soja* which crosses readily with *Glycine max*, and most preferably the Glycine species is *G. max*.

The method of somatic embryogenesis described herein is useful for regenerating whole plants from somatic tissues of soybean and other Glycine species. The term "somatic tissues" refers to tissues not including germ cells or gametes. Somatic tissues are composed of vegetative tissues and cells. "Somatic embryogenesis" means the formation of embryos having a shoot and root axis from somatic tissues or somatic cells which did not contain shoot or root meristematic tissue prior to culturing. "Meristematic tissues" refers to tissues composed of cells capable in nature of producing daughter cells which are differentiated to form specialized tissues. The terms "induction medium, embryo induction medium" and "embryogenesis medium" are used synonymously herein.

In one embodiment of this invention, the cotyledon tissue is cultured on a medium having a high auxin concentration of an auxin from the NAA family. The NAA family is defined herein to include IAA (indole-3-acetic acid), IBA (indole-3-butyric acid), and NAA (alpha-naphthaleneacetic acid). The NAA concentration is preferably at least about 15 mg/l and may be up to at least about 30 to 50 mg/l. The medium should also contain a carbohydrate, preferably selected from the group consisting of sucrose, glucose, fructose, maltose, galactose and xylose, and mixtures thereof, more preferably sucrose, at a concentration of about 3% or less.

In a second embodiment of this invention, a synergistic combination of lowered auxin and lowered carbohydrate may be used for embryo induction. The auxin may be from the NAA family or from the 2,4-D family. The 2,4-D family is defined herein to include 2,4-D (2,4-dichlorophenoxyacetic acid), Picloram (Dow Chemical Co.) (4-amino-3,5,6-trichloropicolinic acid), pCPA (parachlorophenoxyacetic acid), 2,4,5-T (2,4,5-trichlorophenoxyacetic acid), and Dicamba (Sandoz Corporation) (2-methoxy, 3,6- dichloro-o-anisic acid). For purposes of practicing the inventions claimed herein, auxins of similar potency and operational properties to NAA are considered to be in the NAA family and equivalent to NAA. Also, auxins of similar potency and operational properties to 2,4-D are considered to be in the 2,4-D family and equivalent thereto.

Optimal concentrations of auxins of the family 2,4-D in the absence of lowered carbohydrate have been found to be between about 5 and about 10 mg/l, and of the NAA family to be above about 15 mg/l, preferably at least about 30 mg/l. High efficiencies of normal embryo induction occur at 0.5 % w/v carbohydrate even when NAA concentrations are as low as 6.25 mg/l. Efficiencies of embryogenesis have been found by applicants to be inversely proportional to carbohydrate concentration, and it was surprising to find that when auxin concentrations were lowered, embryogenesis efficiency did not generally suffer, but in some cases was improved.

The use of NAA has been found to produce more regenerants having normal morphology than 2,4-D. NAA or an auxin of the NAA family is thus preferred.

In this second embodiment, the carbohydrate (of the types discussed above) should be present at a lowered concentration, preferably about 2% or less, and more preferably about 1.5% or less. A preferred medium comprises about 12.5 mg/l NAA and about 2% sucrose. Another preferred medium comprises about 10 mg/l NAA and about 1.5% sucrose.

The cotyledon tissue preferably includes particularly embryogenic portions as identified in this invention and shown in FIG. 1. These particularly embryogenic portions include cells which give rise to increased numbers of embryos as compared with remaining cotyledonary tissue.

When the embryo induction medium contains an NAA-type auxin, or when the medium contains a 2,4-D type auxin and the tissue is placed adaxial to the medium, the cotyledon portion containing the "fertile crescent" is the particularly embryogenic portion. The "fertile crescent" is defined with reference to FIG. 1. Variability from cotyledon to cotyledon prevents defining this portion in terms of exact measurements; however, this portion will be readily evident to the skilled worker for excision from the cotyledon tissue.

When the embryo induction medium contains a 2,4-D type auxin, and the tissue is placed abaxial to the medium, the cotyledon portion containing the "fertile oval" is the particularly embryogenic portion. Again, the exact measurements of this portion will vary, but will readily be identified and taken from the cotyledon tissue by the skilled worker.

The use of NAA and tissue including the "fertile crescent" is preferred because, among other things, this combination provides the highest efficiency of regeneration of normal plants with embryos more frequently arising from single somatic cells (as opposed to groups of cells).

To ensure maximal contact of the tissue with the regeneration medium (and in transformation processes, with the foreign DNA being used), the tissue is macerated. Maceration is defined herein as a process of wounding the cellular tissue throughout so as to allow maximal contact of wounded tissue with the medium on which the tissue is to be placed, yet preserve a tissue environment for the cells. The wounding should thus not be so radical as to break up the tissue into isolated single cells, yet should be severe enough to ensure that each cell of the tissue comes in contact with the medium. Preferably maceration is accomplished by pressing the tissue into or through a mesh, which may be of any suitable non-toxic material such as stainless steel or nylon, preferably stainless steel. Preferably the mesh is of a fineness so as to break up the tissue into small, visible pieces about ¼ mm² or less, e.g. a mesh size of about 500 μm (No. 35 mesh).

The somatic tissue, preferably after maceration, may be transformed to contain foreign DNA by any means known to the art, preferably by infection with *Agrobacterium tumefaciens* containing the desired foreign DNA, and the transformed tissues cultured to form somatic embryos which are regenerated into whole fertile plants. "Foreign DNA" is any DNA which does not occur naturally at its new location in the host genome. It may consist of DNA or genes with their own promoters or chimeric genes derived from Glycine or other organisms. Preferably, the foreign DNA confers an identifiable phenotype on the regenerated host plant and/or its progeny, by which the transformed plant is distinguishable from naturally-occurring plants. Such phenotypes conferred by foreign DNA include performance on laboratory tests such as Southern, northern, and western blot procedures. By means of this invention whole transformed Glycine plants, preferably *G. max*, are obtained which can express the foreign DNA contained therein, e.g. foreign promoters and enhancers can be expressed so as to operate to turn on and/or enhance the activity of other genes, and foreign genes can be expressed to produce RNA and/or protein.

In the transformation process, maceration of the tissues is preferred prior to contact with the foreign DNA to ensure maximal contact of the cells with the DNA.

Following contact of the tissues to be transformed with the foreign DNA, the tissues are cultured on selection media, all as known to the art. Suitable selection media comprise antibiotics known to the art such as kanamycin, G418, or hygromycin, to which resistance has been conferred to the transformed cells by a corresponding resistance gene.

In a preferred embodiment, no selection agent is used following transformation. This procedure is especially useful with respect to soybean which has low regeneration efficiency when compared with model systems such as tobacco. Since selection agents such as kanamycin inhibit growth even of transformed soybean tissue, and since the resistance genes may be detrimental to the plants, it is desirable to eliminate the use of such selection agents. The increased embryogenesis and transformation efficiency provided by this invention is important to allowing transformation without selection. This efficiency arises as a result of identification and selection of particularly embryogenic portions of the immature cotyledon tissue, especially the "fertile crescent" portion, further as a result of the maceration process which provides maximal contact of all cells of the tissue with the foreign DNA, and still further as a result of the use of NAA which causes high rates of embryogenesis from single cells as opposed to groups of cells, thus ensuring totally transformed regenerants. High percentages of transformed regenerants are produced, and transformation of particular plants can be confirmed by identification of phenotypes conferred by the foreign DNA, such as the presence of foreign DNA as detected on Southern blots.

Transformation is preferably done by means of infection with Agrobacteria containing disarmed Ti-vectors, which may also contain selectable markers. The amount of Agrobacteria used for infection of the plant should be small enough so as not to overgrow the tissue and kill it. Similarly, any selection media used, and antibiotics used to destroy the Agrobacteria once transformation has occurred should be used in concentrations sufficient to accomplish their purpose, but low enough so as not to kill the sensitive Glycine tissue. This is especially important with respect to soybean. Antibiotics useful for destroying Agrobacteria are known to the art, and include cefoxitin, cefotaxime, and carbenicillin.

After somatic embryos have formed from the transformed tissue, they are transferred to suitable media as known to the art for regeneration into whole, fertile transformed plants comprising and capable of expressing the foreign DNA with which they have been transformed. Such regenerated plants and their progeny also comprising and expressing foreign DNA which are phenotypically distinguishable from naturally-occurring plants are included within the subject matter of this invention, and all regenerants produced by the process of this invention and their progeny whether or not they are phenotypically distinguishable from naturally-occurring plants are considered equivalent to such distinguishable plants.

DETAILED DESCRIPTION OF THE PREFERRED EMBODIMENTS

Several embryo induction protocols have been used by applicants to induce somatic embryos and obtain regenerated Glycine plants. A useful protocol for embryogenesis induction is given in P. A. Lazzeri, et al. (1985) supra, incorporated herein by reference. The conditions specified therein are used in the following description unless otherwise specified.

The somatic tissue used herein when it is desired to regenerate wild Glycine species may be stem segments, leaf sections, vegetative tissue of immature flower buds, hypocotyl, or other tissues capable of being maintained in culture. Any suitable regeneration medium known to the art may be used. Many basal media useful in the regeneration medium are known to the art, such as SL, B5, L2 medium, and MS medium. A preferred medium is MS medium. The basal medium should contain an auxin such as an auxin from the NAA or 2,4-D family. For purposes of practicing the inventions claimed herein, auxins of similar potency and operational properties to NAA are considered to be in the NAA family and equivalent to NAA. Also, auxins of similar potency and operational properties to 2,4-D are considered to be in the 2,4-D family and equivalent thereto.

When soybean (*Glycine max*) or *Glycine soja* are being regenerated, the somatic tissues used are preferably cotyledons from immature embryos. Preferably, the seeds containing the immature soybean embryos are between about 2.0 and about 8.5 mm preferably between about 3.0 and about 5.0 mm in length. *G. soja* seeds at comparable maturities are smaller. Preferably, the embryonic axes are removed from the cotyledons, and/or the cotyledons are otherwise wounded. Removal of the embryonic axes insures the somatic nature of the tissue. Test results presented herein show higher embryogenesis frequency when embryonic axes are removed. Dissecting the cotyledons into several pieces, preferably into halves or quarters will also increase embryogenesis frequency. Maceration of the tissues will greatly increase efficiencies.

To be most useful in transformation protocols, the somatic embryos formed should arise from single cells rather than from groups of cells. This will insure that all tissues of the plant regenerated from the single embryonic cell, including the germ cells, will contain the foreign DNA.

For this reason the most embryogenic portions of the cotyledons were identified, as shown in FIG. 1. As detailed in Example 17, to obtain maximal normal embryos on NAA media, peripheral regions of the cotyledons containing the "fertile crescent" should be used, and the tissue should be placed abaxial to the medium. When 2,4-D is used, regions of the cotyledons containing the "fertile oval" can be used, and the tissue should be placed abaxial to the medium. Preferably, however, for a greater number of normal embryos, the tissue should be placed adaxial to the 2,4-D medium and the "fertile crescent" region should be used. Because the NAA provides more "single cell events," that is embryos arising from single cells rather than from clusters of cells, and more normal morphology of regenerated plants, the use of this auxin is preferred, with selection of "fertile crescent" portions of the cotyledon. The embryogenic cells in the identified "fertile" regions are still actively dividing and have not yet differentiated such that they behave like cotyledon cells rather than embryo cells.

To ensure contact of the embryogenic portions of the cotyledon with the media, and enhance regeneration efficiency, preferably tissue containing the embryogenic portions is excised from the cotyledons for culture. The cotyledonary tissue, whether whole cotyledons or excised embryogenic portions are used, is macerated by pushing into or through a mesh. Preferably the mesh is of a fineness, e.g. about 500 $\mu$m (No. 35), such that pieces of cotyledon at most about $\frac{1}{4}$ mm square in size are produced. Regeneration of whole plants from totally isolated single cells is difficult if not impossible, as it appears contact with the tissue environment is necessary for formation of embryos from single cells. At the same time, the more fine the mesh, the more wounding is provided to ensure maximal contact of the cells with the media.

Preferably a number of cotyledons or portions thereof are placed on a conveniently sized piece of mesh, such as 2 cm$^2$ square, which generally accommodate about 20 cotyledons per square. Stainless steel mesh is preferred as providing higher frequency of embryogenesis, although nylon and other suitable, non-toxic materials may also be used. Bronze mesh appears to be toxic to the tissue and is not recommended. The cotyledons may be pushed partly or completely through the mesh, and although it is not necessary, it is convenient to push them partially through the mesh and keep them in the mesh for transference to the medium. To further enhance embryogenesis efficiency, a weak electric current, such as about 2 $\mu$A, can be run through the mesh when conductive (e.g., stainless steel) mesh is used.

The somatic tissues may first be cultured on a medium allowing a degree of dedifferentiation. Such media are known to the art, described for example in J. P. Ranch, et al. (1985), supra. Preferably, however, the tissues are placed directly on the embryogenesis (embryo induction) medium. When "fertile crescent" or "fertile oval" regions are included in the tissue as described below, and the maceration procedures hereof are used, dedifferentiation is not necessary.

The embryo induction media used in this invention for regeneration of soybean and *G. soja* is a basal medium known to the art, containing auxin. The basal medium is preferably MS medium supplemented with B5 vitamins, a carbohydrate source, preferably a sugar such as glucose, sucrose, maltose, galactose, fructose, or xylose, and solidifying agent such as Phytoagar (a trademark of Gibco Company), agar adapted for plant growth or Gelrite (a trademark of Merck & Co., San Diego, Calif.) gellan gum culture medium. The auxin is preferably of the NAA family, and more preferably is NAA. In one embodiment of this invention, NAA is used at concentrations between about 15 mg/l and at least about 30 mg/l to about 50 mg/l. When such high auxin levels are used, carbohydrate concentrations may be as high as about 3% to about 6%. In view of previous generally unsuccessful attempts to use NAA for somatic embryogenesis of soybean, it is surprising to find it produces a higher efficiency of normal embryos at these high concentrations than optimal amounts of 2,4-D, the auxin most successfully used in prior art methods. (Applicants have found that at 5–10 mg/l 2,4-D produces high embryo efficiencies. Above about 10 mg/l, 2,4-D has been found to produce high levels of undesirable soft, friable callus.)

In another embodiment of this invention, NAA at lower concentrations (about 10 mg/l or less) in a synergistic combination with carbohydrate at less than about 2%, preferably about 1.5%, has been found effective. NAA at concentrations up to as high as 50 mg/l have been found to produce normal embryos at high efficiency. NAA at lower concentrations (about 10 mg/l) with lowered carbohydrate has been found to produce more embryos derived from single cells, as opposed to groups of cells, than 2,4-D.

When lower auxin concentrations are used, carbohydrate concentration is preferably at most about 2%, even more preferably at most about 1.5%. Most preferably the carbohydrate concentration is at most about 1%, with concentrations at most about 0.5% also being effective. Surprisingly, it has been found that efficiency of production of normal embryos decreases when carbohydrate concentration increases, and that there is a synergistic effect between lowered auxin concentration and lowered carbohydrate concentration. When low levels of carbohydrate are used, e.g. about 0.5% sucrose, the most normal embryos are obtained at all auxin concentrations tested (up to 50 mg/l) but high levels of efficiency are produced even at relatively low auxin levels (6.25 and 12.5 mg/l NAA), and generally efficiency of production of normal embryos goes down as carbohydrate level goes up at each auxin concentration, with the highest efficiency of normal embryos being produced at 6.25 mg/l NAA and 1.0% sucrose. Preferably, the auxin concentration is at least about 5 mg/l, and the carbohydrate concentration is less than about 2%.

Gelrite gellan gum as a gelling agent at about 0.2% is also preferred in the medium. It is preferred that the pH of the medium be between about 5.0 and 7.0, and more preferably, at most about 5.8 if the medium is unbuffered. If the medium is buffered, it is preferred that the pH be at least about 5.8.

The embryonic culture is preferably placed under low intensity lighting. It is preferred that the light intensity be less than about 80 microEm$^{-2}$s$^{-1}$ (micro Einsteins per square meter per second), and more preferably at most about 10 microEm$^{-2}$s$^{-1}$. The culture may be grown in constant light or the embryogenesis may take place in darkness, but preferably, a 16 hour photoperiod is used. Lamps such as Grolux (a trademark of Sylvania Co.) broad spectrum light source having higher emissions in the blue (430–490 nm) and red (630–680 nm) wave bands are preferred to cool white lamps.

The tissues may be subcultured, but this is not necessary. Once the embryos have formed, e.g. after about 15 to 30 days, they may be moved to a separate maturation medium, but preferably are kept on the embryogenesis medium until mature, i.e. at about 30 days, or when at least about 2.5 mm long. The procedures of P.A. Lazzeri, et al. (1985) supra may be followed.

A shooting medium containing cytokinins known to the art is used to culture the mature embryos. Examples of cytokinins are ADE (adenine sulfate), KIN (6-furylaminopurine), BA (6-benzylaminopurine) also called "BAP" and "6-BA", zeatin, and kinetin. Such a medium could be (1) MS medium containing 0.15 mg/l NAA and 0.033 mg/l of each BA, kinetin and zeatin; (2) the same medium containing only 0.05 mg/l NAA if shoots fail to form after about a month; or (3) 0.017 mg/l each of BA, kinetin and zeatin with 0.05 mg/l NAA. Preferably the last medium is used for all mature embryos, especially when embryos having a well-defined apex are selected for transfer. Once plantlets with primary leaves have been regenerated, they may be transferred to a rooting medium. (In general, in accordance with general usage in the art, when used herein, and unless otherwise specified, the term "plantlet" will mean that leaves, but not roots, have developed.)

Any rooting medium known to the art may be used. An example of a useful medium to which the plantlets may be transferred is a ½ MS 2S medium (×½ macro salts×1 micro salts, B5 vitamins, 2% sucrose, 0.65% Phytoagar agar adapted for plant growth) supplemented with 0.005 mg/l IBA. Preferably the medium contains HPN salts and about 0.25 g/l yeast extract, dissolved in tap water, adjusted to pH about 5.9 before autoclaving and gelled with 0.15% Gelrite gellan gum or 0.65 g/l agar (Difco Bacto-agar). Other HPN medium may be supplemented with either about 5 mg/l coumarin or about 0.005 mg/l IBA for genotypes which do not root readily. Other suitable rooting media are: hydroponic nutrient salt solution (Science 222, 621–623), B5 vitamins, 2% sucrose, Ni 1 μM, 1 mg/l IAA, 9 mg/l coumarin, 0.2% Gelrite gellan gum, or 0.6% Phytogar agar adapted for plant growth, pH 5.9 (before autoclaving); or White's medium-modified White's salt solution, B5 vitamins, 2% sucrose, 0.2% Gelrite gellan gum or 0.6% phytogar Phytoagar agar adapted for plant growth, 1 mg/l IAA, 9 mg/l coumarin, pH 5.9 (before autoclaving). The best rooting took place in the growth chamber under 23 hour day length (100 microEm$^{-2}$s$^{-1}$ at 20° C. and humidity 60%). Preferably the plantlets are grown in isolated containers such as Magenta (trademark of Magenta Co.) sterile clear plastic boxes containing 100 ml rooting media. Light conditions are known to the art, but preferably a 23 hour photoperiod using 50–100 microEm$^{-2}$s$^{-1}$ Grolux broad spectrum light source or cool white fluorescent lamps is used.

When the plantlets have well-developed root systems, they are preferably transferred to pots containing sterilized (e.g. autoclaved or microwaved) potting mix. Preferably, such a potting mix comprises 2:2:1 soil: Promix horticultural soil mix:sand mix. (Promix is a trademark of Premier Brands, Inc., New Rochelle, N.Y.) They are preferably covered to reduce transpiration during the hardening period, and fed with plant food such as Peters complete liquid fertilizer (20:20:20) plant food. (Peters is a trademark of Peters Fertilizer Co., Fogelsville, Pa.) During short days it is desirable to supplement natural light with about 13 hours of artificial (preferably high pressure sodium) light. Mite and whitefly infestations and mildew may be controlled by commercial preparations made for this purpose. See P. A. Lazzeri, et al. (1985), supra.

Transformation methods for introducing foreign genes into plant tissue are well known to the art, described, e.g. in S. H. Mantell, et al., Principles of Plant Biotechnology, An Introduction to Genetic Engineering in Plants (1985), particularly pages 34–57 which are incorporated herein by reference. The following discussions describe preferred embodiments and are not meant to exhaustively describe all means by which Glycine species may be transformed.

Transformation of wild species such as *G. clandestina* and *G. canescens* may be accomplished by using stem, leaf, flower, hypocotyl or other suitable explants. The explants are washed and sterilized, preferably using 70% isopropanol for about one minute, followed by 10% Chlorox plus a drop of Liquinox for about 10 to 15 minutes. The explants are then preferably rinsed with sterile water for about 5 minutes, and this procedure is repeated. Appropriate size pieces into which the tissues are cut are about 1 cm for stem segments, about 1 cm×0.5 cm for leaf sections, and for flower buds, the larger buds are preferably separated into individual pieces, but the immature buds are preferably separated into about 3-bud clusters.

The tissue should be plated onto a regeneration medium, such as an embryogenesis medium as above described, or an organogenic medium. Preferable organogenesis media are: (1) MS salts, B5 vitamins, 3% sucrose, 500 mg/l casein hydrolysate, or 500 mg/l glutamine, 0.5 mg/l NAA, 2.0 mg/l BA (6-benzylaminopurine), 1.0 mg/l kinetin, 0.6% Phytoagar agar adapted for plant growth, at pH 5.9 before autoclaving; or (2) MS salts, B5 vitamins, 3% sucrose, 500 mg/l casein hydrolysate, 0.15 mg/l NAA, 0.33 mg/l 6-BA, 0.33 mg/l kinetin, 0.33 mg/l zeatin, 0.6% Phytoagar agar adapted for plant growth, at pH 5.9 before autoclaving. Preferably about 20 to 30 pieces of tissue are placed on each plate, and the material is then preincubated, preferably for about 1–2 days. Each explant is then inoculated with an Agrobacterium suspension containing a sufficient concentration so as to effectively infect the tissue without killing it, preferably about 0.5 to 1.0 μl of a resuspended overnight culture of Agrobacteria as discussed below. If higher concentrations of Agrobacteria are used, or if the explants are dipped into the bacterial solution, the Agrobacteria will overgrow and kill the explants. The explants are allowed to grow in the presence of the Agrobacteria for several days, e.g. about 1 to about 3 days, then transferred to a regeneration medium as described above which also contains an antibiotic, preferably Mefoxin at a concentration of about 500 mg per ml, to kill off the Agrobacteria. The putatively transformed material is then transferred to a regeneration medium as described above, which may also contain a selection agent corresponding to the selectable marker used in transforming the tissue. Preferably the selection agent is kanamycin, or an analog such as, G418, which will select for transformed tissue carrying a kanamycin resistance (neomycin phosphotransferase II) gene. Kanamycin or G418 are preferably used at a level sufficient to select for transformed tissue without killing it, preferably at about 50 to 300 µg kanamycin per ml, or about 10-50 µg/ml G418.

The transformed explants are then allowed to regenerate as described above. Preferably, they are subcultured at biweekly intervals on a regeneration medium containing the antibiotic and selection agent, until shoot apices are formed, then transferred to appropriate shooting, rooting and soil media.

Transformation of *Glycine max* and *G. soja* may be performed as described above, except that immature cotyledon tissue is used also as described above relative to the discussion of somatic embryogenesis. Preferably the cotyledon tissue has the embryonic axes removed before infection with the Agrobacteria, and more preferably, is macerated as described above, and appropriate embryogenic portions of the tissue are used. Under these preferred conditions, it is not necessary to culture the tissue on dedifferentiation media to form callus before infection. The cotyledons are preferably plated in pairs at a rate of about 10 per 100 mm dish, and are preferably inoculated immediately with Agrobacteria, although inoculation may be delayed several days, if necessary, depending on the genotype being transformed. See Example 21.

The embryogenesis media upon which the cotyledons are plated for transformation may be any embryogenesis media known to the art, such as the media described above containing high auxin concentrations preferably using auxins of the NAA family, or synergistic combinations of low carbohydrate and lowered auxin concentrations. After the cotyledon tissue has been allowed to grow on the embryogenesis medium in the presence of the bacteria for sufficient time to effect transformation, it should be transferred to fresh embryogenesis media containing antibiotics to kill off the bacteria, preferably about 200 to about 500 mg/l, and most preferably about 500 mg/l, Mefoxin (Cefoxitin), Claforan, cefotaxime or carbenicillin. A selection agent such as kanamycin or a kanamycin analog such as G418, or hygromycin, to select for transformed somatic embryos may also be used. For selection, preferable levels in agar of G418 are about 10 mg/l and of kanamycin are about 50 mg/l. When Hygromycin is used, about 2 mg/l is preferred. Gel-rite gum is a preferred gelling agent however, as it appears to provide less stress to the tissues. Tissues are co-cultivated with Agrobacteria for a time sufficient to ensure transformation of a maximum number of cells, but not so long as to cause inordinate tissue death, preferably between about 1 and about 3 days, and most preferably about 1 day.

Because of the possibly adverse effects of selection agents on soybean tissue, and/or possible adverse effects of selectable marker genes such as NPTII on transformed soybean plants, it is most desirable to perform the transformation process without using selection agents. Because of the low regenerability of *G. max* as compared with model systems such as tobacco, the numbers of soybean regenerants will not be overwhelming, and because the maceration procedures described above ensure the contact of virtually all the embryogenic cells with foreign DNA so that relatively few untransformed embryos are formed, and further because the use of NAA and "fertile crescent" portions of the cotyledons means that most of the embryos are derived from single cells, this invention makes it possible in practice to perform effective transformation procedures without using a selection step. After regeneration, transformants may be identified phenotypically by characteristics imparted to the tissue or the regenerated plant by the foreign DNA, including activation of reporter genes such as β-galactosidase or performance on assays such as Southern blotting procedures.

The cultures are preferably subcultured about every 28-30 days onto embryogenesis media plus antibiotics (with or without selection agents) until the somatic embryos are formed, then transformed to shooting media, rooting media and potting mix as described above. The cultures should be maintained with antibiotics and if selection agents are being used, they should be continued.

The Agrobacteria containing the vector to be used to insert foreign genes into the plant tissue are cultured by means known to the art, preferably by growing on a plate of appropriate medium, preferably YEP medium (10.0 g/l yeast extract, 10.0 g/l peptone, 5.0 g/l NaCl, 15 g/l agar, at pH 7.0), containing selection agents at about 28 degrees C. The marker used in the vector may be a kanamycin resistance gene, and the selection agent would therefore be kanamycin or G418. The marker may be any marker known to the art, and the medium will be adjusted accordingly to select only for Agrobacteria carrying the vector.

Agrobacterium colonies are scraped off the medium and suspended in appropriate media such as YEP broth or minimal medium. Preferably about 25 to 50 colonies are suspended per 1.5 ml of medium. After overnight suspension, a loop of the material is streaked out onto an appropriate medium, such as YEP medium containing the appropriate antibiotics, to give single colonies. A single colony is used to inoculate about 25 ml of the appropriate broth medium, again preferably YEP, containing appropriate antibiotics. The culture is grown overnight at about 28 degrees C., preferably in a shaking water bath. The cultures are spun down to harvest the cells, which are resuspended in broth or minimal medium. About 0.5 to 1.0 µl of this resuspended overnight culture is used to inoculate the plant tissue to be transformed, as described above. The culture solution used to inoculate the plant tissue should contain a relatively low concentration of Agrobacteria, preferably no more than about $10^4$ to $10^8$ organisms per ml, and more preferably no more than about $10^6$ organisms per ml.

Methods for transforming Agrobacteria, and vectors for doing so are described in detail in many references, see, e.g. S. H. Mantell, et al. (1985), supra, particularly Chapter 4 thereof, and the references referred to therein. The vector used for transforming the plant tissue in this invention need not be an Agrobacterium vector, but is preferably an Agrobacterium vector. Preferably the vector contains a marker gene allowing for selection of transformants, and preferably this marker gene is a kanamycin resistance gene. Many such vectors are commercially available, or have been reproducibly described in the literature, and may be used to transform soybean and other Glycine species. Preferably the vector also contains a gene coding for a desirable trait, such as herbicide, e.g. glyphosate, resistance. See, e.g., D. M. Shah, et al. (1986), "Engineering Herbicide Tolerance in Transgenic Plants," Science 233:478-481. Glycine tissues may be transformed by any vector known to the art to be capable of transforming such plant tissues, and when appropriate markers and selection procedures are provided as discussed herein, and as known to the art, selected transformed tissue may be regenerated into whole fertile plants by the methods of this invention.

The vector used in a preferred embodiment was pH5pZ3D, comprising a zein gene under control of a β-phaseolin promoter, all as more fully described in L. Hoffman (1987) EMBO 6(11):3211-3222, incorporated herein by reference. This vector is available from the author upon request as is required for publication in said journal. The vector was placed in *Agrobacterium tumefaciens* strain LBA4404, described in Hoekema et al. (1983) Nature 303:179. This is a widely available strain, also available from the authors.

Methods of regenerating Glycine plants, and preferably soybean, have been described. These methods provide the necessary efficiency to allow for analysis of somaclonal variation among regenerants, and to allow for regeneration of transformed tissue into whole, fertile plants containing and reproducing foreign DNA in themselves and in progeny plants.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

EXAMPLES

Note: Comparisons of treatments may only be made within and not between experiments as all "control" treatments were not necessarily identical.

EXAMPLE 1

Effects of various hormones on embryogenesis

Plant Growth, Embryo Isolation

Procedures for donor plant growth, pod sterilization and embryo isolation were as described previously (P. A. Lazzeri, D. F. Hildebrand and G. B. Collins, Plant Mol. Biol. Reporter, 3 (1985) 160). Briefly, plants were grown in pots in a greenhouse, with natural light supplemented with 13 hours artificial (high pressure sodium) light during winter months. Pods containing seeds of length 4.0+1.0 mm were surface-sterilized by 30 sec immersion in 70% isopropyl alcohol, followed by 10 min in 25% Chlorox bleach and then two rinses in sterile water. Pods were opened and embryos isolated from the immature seeds.

Media, Culture Conditions

The basal medium consisted of MS salts (T. Murashige and F. Skoog, Physiol. Plant, 15 (1962) 473), B5 vitamins (O. L. Gamborg, R. A. Miller and K. Ojima, Exp. Cell, Res., 50 (1968) 151), 3% sucrose and 0.65% Phytoagar, (a trademark of Gibco Co.) agar adapted for plant growth at pH 5.9 before autoclaving. Hormones were added to media before autoclaving, with the exception of ABA, which was filter-sterilized. Embryos (or cotyledon pairs) were cultured at 10 per 30 ml of medium in 20×100 mm plastic dishes, at 25°±3° C. under a 16 hour photoperiod of cool white fluorescent light (20 microEm$^{-2}$s$^{-1}$).

Culture Assessment

Cultures were scored at 30d (d=days). Six parameters were used to assess embryo response: I. Embryogenesis Frequency, =number of embryogenic cultures/total cultures initiated, II. Mean Embryo Number, =mean number of somatic embryos (both "normal" and "abnormal") per embryogenic culture, III. Efficiency, =Embryogenesis Frequency×Mean Embryo No., IV. Frequency of Normal Embryos, =number of cultures with normal embryos/total embryogenic cultures, V. Rooting Frequency, =percentage of cultures with roots, and VI. Callusing Frequency, =percentage of cultures developing callus.

For assessment, embryos with distinct root and shoot poles and at least one defined cotyledon were classed as "normal, while embryos lacking distinct shoot poles, without cotyledons or with fused cotyledons were classed as "abnormal Bipolar structures fused to parental cotyledon tissue were not scored unless a distinct shoot apex was present, in which case they were classed as abnormal embryos.

A minimum of 60 embryos was cultured per treatment, and generally ≧100 embryos were used per treatment.

The effects of hormones on somatic embryogenesis efficiencies were investigated as shown in Table 1. Seventeen *G. max* genotypes as follows were tested and the results were pooled: maturity group 00 cultivars Acme, Ada, Agate, Altona, Crest, Flambeau, Hidatsa, Manitoba Brown, McCall, Morsoy, Norman, Ogemaw, Pagoda, Pando, Portage, Sioux, and group IV genotype PI 408.294A. Whole embryos were cultured.

Somatic embryogenesis was dependent on the type and concentration of auxin in the medium (somatic embryos have never been observed in the absence of exogenous auxin, throughout several experiments). Of the auxins IBA, NAA, and 2,4-D, the last was most potent for somatic embryo induction (Table 1), and gave the highest efficiency values at each concentration (efficiency is a measure of the yield of somatic embryos per zygotic embryo cultured). For each auxin, embryogenesis frequency increased with auxin concentration. Mean embryo number showed a similar, but less marked trend.

There was a clear effect of auxin type on culture morphology. Somatic embryos induced by NAA had the most normal morphology although mono- and polycotyledonous embryos were common. 2,4-D-induced embryos were usually horn shaped but at high auxin concentrations (5 and 10 mg/l) leafy and fasciated structures became more common. Embryos induced on IBA were generally incompletely developed, especially at lower auxin concentrations. Cultures on NAA or IBA media produced little callus whereas 2,4-D invariably induced some callusing. Roots were usually formed on IBA and NAA media, but rarely on 2,4-D.

When tested in combination with 5 mg/l NAA, BA at 0.01 mg/l had little effect, while 0.05 mg/l BA reduced embryogenesis frequency. The higher BA concentration also stimulated callus production. ABA at 0.1 mg/l, in combination with 5 mg/l NAA, depressed embryogenesis in comparison with media containing NAA alone.

A further comparison of four NAA concentrations between 5.0 and 12.5 mg/l utilizing McCall genotype (Table 2) suggested that the efficiency of embryogenesis was increased by concentrations above 5 mg/l, but that the frequency of normal embryos decreased at higher auxin levels. Whole embryos were used. In the same experiment 5 mg/l 2,4-D gave more than double the efficiency value of the most effective NAA medium, but with a low frequency of normal embryo production. In combinations of 5 mg/l NAA with 0.05, or 0.5 or 5.0 mg/l 2,4-D, the two lower 2,4-D levels had a slight depressive effect on embryogenesis efficiency while the high level gave results very similar to those for 5 mg/l 2,4-D alone (Table 2). In each combination 2,4-D appeared to be the "dominant" auxin in terms of somatic embryo morphology, even 0.05 mg/l 2,4-D markedly reduced the frequency of normal embryo production by comparison with N5 medium (5 mg/l NAA) without 2,4-D. Hereinafter "N" followed by a number refers to that number of mg/l NAA. "D" followed by a number refers to that number of mg/l 2,4-D.

ABA at 0.1 mg/l, in combination with 5 mg/l 2,4-D, had little influence on embryogenesis efficiency but increased the frequency of normal embryos slightly over the control value (plain D5 (5 mg/l 2,4-D) medium). At 1.0 mg/l, however, ABA halved the embryogenesis efficiency and reduced normal embryo production. An occasional effect of ABA on the morphology of 2,4-D-induced somatic embryos was to make their cotyledons broad and leaf-like.

Table 3 shows the effects of high concentrations of NAA on somatic embryogenesis. Isolated cotyledons taken from J103 (Jacques Seed Co., Wisconsin) and McCall were tested giving similar results. Data for J103 only is presented.

The data here show the importance of exogenous auxin in regulating soybean somatic embryogenesis. Auxin type and concentration had specific and distinct effects on the process in terms of efficiency (embryogenesis frequency and mean embryo number). Media containing 2,4-D gave the highest embryogenesis efficiency values; at equivalent concentrations NAA and IBA were progressively less active (Table 1, 2 and 3). This high potential for embryo induction is shared by other phenoxyacetic acids such as cCPA and 2,4,5-T. With each auxin examined, embryogenesis efficiency increased with increase in concentration. Variation in embryogenesis efficiency with auxin type or concentration (and with other treatments) generally reflected similar responses of the two constituent parameters (Tables 1, 2 and 3). For NAA, concentrations between 1 and 30 mg/l were tested, with 30 mg/l giving the highest efficiency, suggesting this level may still be sub-optimal. For 2,4-D, embryogenesis efficiency increased with auxin concentration but there was a concomitant increase in friable callus formation and in dedifferentiation of early somatic embryos, so the optimum was between 5 and 10 mg/l. This effect was exaggerated in cultures of small embryos and isolated cotyledons. In other studies on soybean somatic embryogenesis, 2,4-D has been the most commonly used auxin (W. D. Beversdorf et al. (1977), supra, G. C. Phillips, et al., supra, M. L. Christianson, et al., supra, J. P. Ranch, et al. (1985), supra, B. J. Li, et al., supra), although only two studies compared embryogenesis frequency with different auxins B. Lippman, et al. (1984), supra, U. B. Barwale, et al. (1986), supra). Both of these investigations found 2,4-D to be the most active auxin. Where different 2,4-D concentrations have been tested, the optima found have differed (1 mg/l (B. Lippman, et al. (1984), supra), 5 mg/l (J. P. Ranch, et al. (1985), supra), 10 mg/l, (Table 1 hereof)). These discrepancies may stem from the use of different sucrose levels or different explants (whole embryos versus isolated cotyledons), as both factors strongly affect embryogenesis. Similarly, the optimal NAA concentration suggested by the present study (30 mg/l) contrasts with the optima of other studies (0.5 mg/l—B. Lippman, et al. (1984), supra; 8 mg/l—U. B. Barwale, et al. (1986), supra).

Somatic embryo induction required only auxin as a hormone source; in treatments where either cytokinin (BA) or ABA was also supplied embryogenesis efficiency was either unaffected or reduced, depending on supplement concentration (Tables 1 and 2). An inhibitory effect of cytokinin on soybean somatic embryogenesis has previously been reported (L. B. Lippman et al. (1984), supra), although other embryogenesis protocols include periods of cytokinin exposure (W.D. Beversdorf, et al. (1977), supra, M. L. Christianson, et al. (1983), supra, B. J. Li, et al. (1985), supra). ABA appears to regulate soybean embryogenesis in vivo (R. C. Ackerson, J. Exp. Bot., 35 (1984) 403.), and either stimulates or inhibits zygotic embryo growth and development in vitro, depending on embryo stage (R. C. Ackerson, J. Exp. Bot., 35 (1984) 414). The present data suggest, however, that ABA inhibits auxin-induced somatic embryogenesis, although an influence on somatic embryo morphology was observed in that cotyledons of some 2,4-D-induced embryos became leaf-like.

The question of soybean somatic embryo "quality", or morphological normality, has been discussed by several investigators (W. D. Beversdorf, et al. (1977), supra, M. L. Christianson, et al. (1983), supra, B. Lippman, et al. (1984), supra, J. P. Ranch, et al. (1985), supra, U. B. Barwale, et al. (1986), supra), but no previous study has attempted to quantify the frequencies of normal and abnormal embryos. This parameter is, however, of prime importance to the application of embryogenesis systems as the efficiency of conversion from embryos to plants varies considerably with embryo normality (J. P. Ranch, et al. (1985), supra, P. A. Lazzeri, et al. (1985), supra. U. B. Barwale, et al. (1986), supra). The major factors affecting soybean somatic embryo morphology are auxin type and concentration (B. Lippman, et al., (1984), supra, J. P. Ranch, et al. (1985), supra, U. B. BarWale, et al. (1986), supra), although other physical, chemical and nutritional factors are also important. An effect of auxin type on somatic embryo morphology is seen in the differences between embryos induced by 2,4-D or other phenoxyacetic acids (pCPA, 2,4,5-T) and those induced by "non-phenoxy" auxins (NAA, IBA). Embryos induced by 2,4-D are generally horn-shaped, leafy or fasciated with indistinct cotyledons. They often lack a defined root pole and the shoot apex is frequently undeveloped in otherwise "mature" embryos. In contrast, NAA-induced embryos usually have distinct bipolarity, with clear radicle and hypocotyl regions, well-defined cotyledons and a shoot apex visible from an early stage of development. These gross differences in morphology are reflected in the ease with which embryos may be "germinated" NAA-induced embryos germinate readily (U. B. Barwale, et al. (1986), supra) while 2,4-D-induced embryos are recalcitrant (W.D. Beversdorf, et al. (1977), supra, B. Lippman, et al., (1984), supra) and often require extended periods of incubation (P. A. Lazzeri, et al. (1985), supra) or complicated cultural manipulations (J. P. Ranch, et al. (1985), supra), for germination. The consensus of other studies (W.D. Beversdorf, et al. (1977), supra, M. L. Christianson, et al. (1983), supra, B.

Lippman, et al., (1984), supra, J. P. Ranch, et al. (1985), supra, U. B. Barwale, et al. (1986), supra) supports these observations, with the reservation that other workers have been unable to produce viable embryos on both NAA and 2,4-D media (B. Lippman, et al., (1984), supra, U. B. Barwale, et al. (1986), supra): so the present study is the only one in which comparisons have been made under the same experimental conditions.

In the present study, elevated NAA concentrations gave the highest yields of normal embryos, while high concentrations of 2,4-D gave very low yields of normal embryos. In contrast, Ranch et al. (1985), supra found that embryo normality increased at high 2,4-D concentrations. The two studies differ in that the former observations are based on primary cultures, while the latter observations were made on secondary cultures previously selected for organized growth on 2,4-D. In alfalfa, it has been shown that somatic embryos induced on low 2,4-D concentrations have more normal morphology and seed storage protein profiles and have a higher frequency of conversion to plantlets than those induced on high 2,4-D concentrations (D. A. Stuart, J. Nelson, S. G. Strickland and J. W. Nichol, "Factors Affecting Developmental Processes in Alfalfa Cell Cultures," in: R. R. Henke, K. W. Hughes, M. P. Constanin and A. Hollaender (Eds.), Tissue Culture in Forestry and Agriculture, Plenum, N.Y., 1985, p. 59.).

In media containing both 2,4-D and NAA, 2,4-D had the dominant effect on somatic embryo morphology (Table 2). A combination of NAA and 2,4-D was used previously (W. D. Beversdorf, et al. (1977), supra) and abnormal, horn-shaped embryos were reported. In the work here, ABA modified the morphology of 2,4-D-induced embryos (Table 2), making their cotyledons leaf-like.

TABLE 1

Effects of Hormones on Somatic Embryogenesis (Pooled data, 17 genotypes, whole embryos cultured).

| Hormone Concn. (mg/l) | Embryogenesis Frequency | Mean Embryo No. (B)[1] | Efficiency (A × B) |
|---|---|---|---|
| IBA 1.0 | 7.0% | 1.80 ± 0.58 | 0.13 |
| IBA 2.5 | 11.3% | 1.22 ± 0.19 | 0.14 |
| IBA 5.0 | 17.4% | 1.33 ± 0.14 | 0.23 |
| IBA 10.0 | 17.1% | 1.33 ± 0.19 | 0.23 |
| NAA 1.0 | 12.5% | 1.75 ± 0.31 | 0.22 |
| NAA 2.5 | 15.4% | 1.09 ± 0.09 | 0.18 |
| NAA 5.0 | 28.3% | 1.41 ± 0.19 | 0.40 |
| NAA 10.0 | 38.7% | 1.72 ± 0.21 | 0.67 |
| 2,4-D 1.0 | 20.3% | 2.08 ± 0.95 | 0.42 |
| 2,4-D 2.5 | 24.3% | 1.82 ± 0.32 | 0.44 |
| 2,4-D 5.0 | 39.1% | 2.56 ± 0.54 | 1.00 |
| 2,4-D 10.0 | 46.8% | 3.83 ± 0.58 | 1.80 |
| NAA 5.0, BAP 0.01 | 23.2% | 1.69 ± 0.33 | 0.39 |
| NAA 5.0, BAP 0.05 | 10.1% | 1.71 ± 0.36 | 0.17 |
| NAA 5.0, ABA 0.1 | 11.8% | 1.38 ± 0.18 | 0.16 |

[1] In this and subsequent tables, Mean Embryo No. data are presented as means and standard errors of the means.

TABLE 2

Effects of NAA, 2,4-D and ABA on somatic Embryogenesis (cv McCall, whole embryos cultured).

| Hormone Concn. (mg/l) | Embryogenesis Frequency (A) | Mean Embryo No. (B) | Efficiency (A × B) | Frequency of Normal Embryos |
|---|---|---|---|---|
| NAA 5.0 | 29.3% | 1.73 ± 0.21 | 0.51 | 27.3% |
| NAA 7.5 | 36.3% | 2.24 ± 0.26 | 0.81 | 20.7% |
| NAA 10.0 | 32.9% | 2.52 ± 0.37 | 0.83 | 26.1% |
| NAA 12.5 | 37.1% | 2.08 ± 0.37 | 0.78 | 15.4% |
| NAA 5.0, 2,4-D 0.05 | 24.0% | 1.72 ± 0.41 | 0.41 | 16.7% |
| NAA 5.0, 2,4-D 0.5 | 16.0% | 1.67 ± 0.22 | 0.27 | 16.7% |
| NAA 5.0, 2,4-D 5.0 | 56.0% | 3.69 ± 0.35 | 2.07 | 11.9% |
| 2,4-D 5.0 | 60.0% | 3.40 ± 0.35 | 2.04 | 12.6% |
| 2,4-D 5.0, ABA 0.1 | 61.3% | 2.85 ± 0.30 | 1.75 | 17.4% |
| 2,4-D 5.0, ABA 1.0 | 41.4% | 2.45 ± 0.29 | 1.02 | 3.4% |

TABLE 3

Effects of High Concentrations of NAA on Somatic Embryogenesis (cv J103, isolated cotyledons cultured).

| Auxin Concn. (mg/l) | Embryogenesis Frequency (A) | Mean Embryo No. (B) | Efficiency (A × B) | Frequency of Normal Embryos | Rooting Frequency | Callusing Frequency |
|---|---|---|---|---|---|---|
| NAA 10 | 85.0% | 2.47 ± 0.18 | 2.10 | 35.3% | 23.3% | 48.3% |
| NAA 20 | 96.3% | 2.65 ± 0.17 | 2.55 | 34.6% | 48.1% | 68.5% |
| NAA 30 | 93.2% | 2.82 ± 0.17 | 2.63 | 38.2% | 57.6% | 84.7% |

EXAMPLE 2

Effects of Subculture Frequency on Somatic Embryogenesis

Since increasing NAA concentrations gave relatively small increases in embryogenesis efficiency (Table 2), the effects of subculture frequency (i.e. the provision of non-depleted medium) were examined (Table 4). McCall genotype was tested, and whole embryos were cultured following the procedures set forth in Example 1.

Cultures were initiated on medium containing 5 or 10 mg/l NAA and subcultured to fresh medium of the same composition at intervals of 5, 10 or 15d. The total culture period was 30d so cultures were transferred either five, two or one times, with control cultures having the standard incubation period.

In N10 medium embryogenesis efficiency showed little variation between treatments, while in N5 medium efficiency values were slightly higher in the 5d and 10d subculture treatments. In N5 medium normal embryo production was low throughout, while in N10 medium the 15d subculture treatment produced the most normal embryos.

In the two NAA-media tested (N5 and N10), subculture frequency had little effect on embryogenesis, and efficiency levels were consistently lower than those obtainable with high NAA concentrations (20-30 mg/l). These data suggest that auxin depletion is not a factor limiting embryogenesis, but that a steep auxin gradient between the medium and the explant is desirable. Soybean cotyledon tissue has a high diffusive resistance (R. M. Gifford and J. H. Thorne (1985) Plant Physiol. 77:863), so a high external auxin concentration may be needed for concentrations to develop within the explant.

In a later study in which cultures were initiated on medium containing 10 mg/l NAA, it was found that about a 7-day rather than a 30-45 day total exposure period was preferred. Decreasing the exposure time to about a week approximately doubled the number of embryos produced and these were healthier and had a higher respiration rate.

It appears that 2,4-D's properties of high productivity and abnormal morphology induction may not easily be separated.

Among the 2,4-D to NAA transfer treatments embryogenesis efficiency increased with length of exposure to 2,4-D from 1d to 5d and then decreased at 10d. [In this experiment the embryogenesis frequency in the D5 30d treatment was lower than routinely expected from isolated cotyledons on this medium, although the mean embryo number was quite typical.] The frequency of normal embryos was highest in treatment D5 30d and lowest on D5 10d. The single NAA to 2,4-D treatment gave the lowest efficiency value and like the D5 30d treatment yielded no normal somatic embryos. Root production was reduced by the presence of 2,4-D during more than 10d of the culture period, while callusing showed a positive correlation with length of exposure to 2,4-D.

In a second "transfer" experiment cultures were initiated on N10, N20 or N30 medium and were then transferred to fresh N10 medium after 5, 10 or 15d, or were left on the original medium throughout the 30d culture period. Embryogenesis frequency was similar among all treatments, but cultures on N20 and N30 media gave consistently higher mean embryo number values (N20, mean 4.07, range 3.83-4.27; N30, mean 4.77, range 4.48-5.00) than N10 medium (mean 3.62, range 3.05-4.12), and the N30 30d treatment induced most normal embryos (40.5%). The time of incubation before transfer had no consistent effect on embryogenesis efficiency. Differentials between the three levels of NAA concentration were more marked than in the experiment summarized in Table 3. However, the highest frequency of normal embryo production again occurred on N30 medium. Both root and callus production were stimulated by elevated NAA levels.

TABLE 4

Effects of Subculture Frequency on Somatic Embryogenesis (cv McCall, whole embryos cultured).

| Auxin Concn. (mg/l) | Subculture Frequency | Embryogenesis Frequency (A) | Mean Embryo No. (B) | Efficiency (A × B) | Frequency of Normal Embryos |
|---|---|---|---|---|---|
| NAA 5 | 5d | 55.6% | 2.13 ± 0.21 | 1.18 | 3.3% |
|  | 10d | 53.3% | 2.34 ± 0.21 | 1.29 | 9.4% |
|  | 15d | 50.0% | 1.96 ± 0.22 | 0.98 | 0 |
|  | No Subculture | 46.7% | 1.93 ± 0.17 | 0.90 | 3.6% |
| NAA 10 | 5d | 51.7% | 2.00 ± 0.17 | 1.03 | 6.5% |
|  | 10d | 60.0% | 1.70 ± 0.15 | 1.02 | 13.3% |
|  | 15d | 47.3% | 2.23 ± 0.19 | 1.05 | 19.2% |
|  | No Subculture | 48.0% | 2.08 ± 0.22 | 1.00 | 16.7% |

EXAMPLE 3

Effects of Transfers Between 2,4-D and NAA Media on Somatic Embryogenesis

The effects of either initial culture on high concentrations of NAA (20 or 30 mg/l), or of various periods on 5 mg/l 2,4-D, before transfer to "standard" medium (10 mg/l NAA) were investigated. Isolated cotyledons were cultured according to the methods set forth in Example 1. The results are set forth in Table 5. Both J103 and McCall were tested, giving similar results. Data from J103 only is given.

The efficiency of somatic embryogenesis on NAA medium was increased by 3 or 5d preincubation on 2,4-D medium, but this increase in embryo production was, with the exception of the 2,4-D 1d treatment, accompanied by a reduction in normal embryo frequency.

TABLE 5

Effects of Transfers between 2,4-D and NAA media on Somatic Embryogenesis (cv J103, isolated cotyledons cultured).

| Treatment (medium/days) | Embryogenesis Frequency (A) | Mean Embryo No. (B) | Efficiency (A × B) | Frequency of Normal Embryos | Rooting Frequency | Callusing Frequency |
|---|---|---|---|---|---|---|
| N10 30d | 80.0% | 3.18 ± 0.35 | 2.54 | 37.5% | 52.5% | 30.0% |
| D5 30d | 62.5% | 3.48 ± 0.51 | 2.18 | 0 | 0 | 97.5% |
| D5 1d, N10 29d | 72.0% | 2.56 ± 0.25 | 1.84 | 38.9% | 80.0% | 62.0% |
| D5 3d, N10 27d | 85.7% | 3.67 ± 0.24 | 3.14 | 19.0% | 79.6% | 63.3% |
| D5 5d, N10 25d | 92.0% | 3.89 ± 0.22 | 3.58 | 29.1% | 72.0% | 98.0% |
| D5 10d, N10 20d | 44.9% | 3.23 ± 0.43 | 1.45 | 9.1% | 0 | 100% |
| N10 5d, D5 25d | 52.0% | 2.19 ± 0.43 | 1.14 | 0 | 0 | 75.6% |

EXAMPLE 4

Effects of Embryo Size on Somatic Embryogenesis

Using the procedures of Example 1, the influence of embryo size on response in culture was investigated in two experiments. In the first, embryos from seeds ranging from 1.5 to 8.5 mm long were compared. Cultures from seeds between 2.5 and 4.0 mm long were found to be most responsive and this size range was further studied. In this experiment embryos of four size classes, 2.5, 3.0, 3.5 and 4.0 mm (length of immature seed to nearest 0.5 mm) were cultured on the first twelve media of Table 1. Seventeen genotypes were used, with the n value for each embryo size class being ≧240. Results are set forth in Table 6.

Embryo size had an important influence on somatic embryogenesis. Although embryos from seeds ranging in length from 1.5 to 8.5 mm were responsive, those from seeds between 2.5 and 4.0 mm long were most productive. Within this range, embryos from seeds 4.0±0.5 mm had the highest embryogenesis frequency and mean embryo number values. In general, small embryos (seed length≦2.0 mm) tended to form soft, gelatinous callus, while large embryos (seed length≧6.0 mm) often showed no response or, in the presence of low auxin levels, tended to germinate.

Other studies have reported similar optimal size ranges (B. Lippman, et al., (1984), supra, J. P. Ranch, et al. (1985), supra, U. B. Barwale, et al. (1986), supra), but it is not possible to make direct comparisons because of differences in the genotypes and growth environments used.

TABLE 6

Influence of Embryo Size on Somatic Embryogenesis
(Pooled data from 17 genotypes, whole embryos cultured on the first 12 media of Table 1.)

| Embryo Size Class* | Embryogenesis Frequency (A) | Mean Embryo No. (B) | Efficiency (A × B) |
|---|---|---|---|
| 2.5 mm | 16.6% | 1.81 ± 0.26 | 0.30 |
| 3.0 mm | 14.9% | 1.92 ± 0.21 | 0.29 |
| 3.5 mm | 18.9% | 1.78 ± 0.22 | 0.34 |
| 4.0 mm | 27.6% | 2.05 ± 0.25 | 0.57 |

*Length of whole immature seed to nearest 0.5 mm.

EXAMPLE 5

Effects of Genotype on Somatic Embryogenesis

The influence of genotype on somatic embryogenesis was examined in 17 maturity-group 00 soybean cultivars and one group IV genotype, PI 408.294A. The procedures of Example 1 were followed using whole embryos. Embryos were cultured on the first 12 media of Table 1; data pooled over all media are presented in Table 7. Data for J103 is similar to that of McCall and is not given.

Of the seventeen soybean genotypes compared, all but one, cv Agate, yielded embryogenic cultures (Agate was, however, responsive in later experiments). There was considerable variation among genotypes in both embryogenesis frequency and mean embryo number; the most productive cultivar (Ogemaw) had an efficiency value more than six times that of the least productive (Acme). Despite this variation in somatic embryo production, the gross morphology of the process appeared identical over all genotypes, although there was variation in the proportion of normal to abnormal somatic embryos.

Throughout these experiments, donor plants were maintained under as close to identical conditions as possible. There was, however, noticeable seasonal variation in plant growth and culture response. Summer-grown plants were most prolific and their embryos appeared more responsive in culture (although this effect has not yet been critically examined). The major environmental variables between summer and winter months were irradience level and quality.

While there was variance in the embryogenesis efficiency obtained from different soybean genotypes, to date all lines tested have given some level of embryogenesis, suggesting that the process is not genotype-specific. This conclusion is supported elsewhere (B. Lippman, et al., (1984), supra, J. P. Ranch, et al. (1985), supra, U. B. Barwale, et al. (1986), supra). Although yet other studies do report genotype effects, these may result from the use of sub-optimal conditions for embryogenesis (W.D. Beversdorf, et al. (1977), supra, U. B. Barwale, et al. (1986), supra). A negligible genotype effect on regenerability has major implications for the application of the system in soybean improvement (D. F. Hildebrand, et al. (1985), supra), in that regeneration protocols should be directly applicable to elite soybean breeding lines.

TABLE 7

Somatic Embryogenesis from Seventeen Soybean Genotypes (Pooled data from 12 media, whole embryos cultured).

| Genotype | Embryogenesis Frequency (A) | (ranking) | Mean Embryo No. (B) | (ranking) | Efficiency (A × B) |
|---|---|---|---|---|---|
| Acme | 11.2% | (15) | 1.20 ± 0.20 | (14) | 0.13 |
| Ada | 13.4% | (14) | 3.44 ± 0.90 | (1) | 0.46 |
| Agate | 0 | (17) | 0 | (17) | 0 |
| Altona | 22.3% | (6) | 1.00 ± 0.99 | (15) | 0.22 |
| Crest | 24.6% | (3) | 1.72 ± 0.23 | (11) | 0.42 |
| Flambeau | 14.3% | (13) | 1.00 ± 0.68 | (16) | 0.14 |
| Hidatsa | 18.8% | (10) | 2.00 ± 0.82 | (7) | 0.38 |
| Manitoba Brown | 22.7% | (5) | 3.20 ± 0.86 | (2) | 0.73 |
| Morsoy | 17.8% | (11) | 1.75 ± 0.41 | (10) | 0.31 |
| Norman | 5.8% | (16) | 2.33 ± 0.88 | (6) | 0.14 |
| Ogemaw | 28.8% | (1) | 2.79 ± 0.86 | (3) | 0.80 |
| Pagoda | 16.4% | (12) | 2.36 ± 0.69 | (5) | 0.39 |
| Pando | 21.7% | (7) | 1.46 ± 0.24 | (13) | 0.32 |
| Portage | 23.6% | (4) | 2.67 ± 1.12 | (4) | 0.63 |
| Sioux | 25.0% | (2) | 1.88 ± 0.44 | (8) | 0.47 |
| McCall | 20.3% | (8) | 1.65 ± 0.13 | (12) | 0.33 |

TABLE 7-continued

Somatic Embryogenesis from Seventeen Soybean Genotypes (Pooled data from 12 media, whole embryos cultured).

| Genotype | Embryogenesis Frequency (A) | (ranking) | Mean Embryo No. (B) | (ranking) | Efficiency (A × B) |
|---|---|---|---|---|---|
| PI 408.294A | 19.0% <br> 18.0 ± 1.77% | (9) | 1.79 ± 0.25 <br> 1.90 ± 0.21 | (9) | 0.34 <br> 0.37 ± 0.05 |

EXAMPLE 6

Effects of Salt Compositions and Nitrogenous Compounds on Somatic Embryogenesis Using the general procedures of Example 1, the effects of three medium salt compositions and of three nitrogen sources were examined in cultures of ten genotypes. B5 (O. L. Gamborg, et al. (1968), supra) and L2 (G. C. Phillips and G. B. Collins, Crop Sci., 19 (1979) 59) were compared with the standard MS salts. Supplements of ammonium nitrate (1.65 g/l) or glutamine and methionine (8.5 g/l and 1.5 g/l) were tested in B5 salts, and casein hydrolysate (Difco enzymic digest, 0.5 g/l) was tested in MS salts. Results are set forth in Table 8. In a second experiment, investigating the effects of supplementary nitrogenous compounds, a range of amino acids and polyamines was compared using both McCall and J103 genotypes. Results were similar for both genotypes, and data from McCall only is given. Results are set forth in Table 9. Glutamine, methionine, proline and arginine were all supplied singly at 20 mM; glutamine and methionine were supplied in combination, each at 10mM; the polyamines spermine, spermidine and putrescine were supplied singly at 1 mM; and casein hydrolysate was supplied at 0.5 g/l. With the exception of casein hydrolysate all compounds were added as filter-sterilized solution (pH 5.5) to cooling medium.

When MS, L2 and B5 salts were compared (Table 8), embryogenesis efficiency was markedly lower on the last composition. Supplementing B5 salts with extra reduced nitrogen, either in the form of $NH_4NO_3$, or of glutamine and methionine, raised the embryogenesis efficiency to a level comparable to that of MS or L2 media, with the amino nitrogen supplement being most effective. The addition of amino nitrogen, as casein hydrolysate, to MS salts increased the mean embryo number and raised embryogenesis efficiency in comparison with unsupplemented medium. The effects of supplementary nitrogen compounds were further investigated in the experiment shown in Table 9. In this study, when supplied at 20mM in N10 medium (MS salts, 10 mg/l NAA) four amino acids and casein hydrolysate (0.5 g/l) all depressed embryogenesis to varying degrees. Similar results were observed in media containing polyamines (at 1 mM). The frequencies of normal embryos were also depressed in supplemented media. Variation in embryogenic response appeared to be exaggerated in supplemented media, and with two particular supplements, the polyamines spermidine and putrescine, extremely prolific cultures, bearing numbers (5-15) of normal embryos were occasionally produced. An effect of some compounds, notably proline, glutamine and casein hydrolysate, was to increase chlorophyll levels and to induce the leaching of dark-pigmented compounds which may have been phenolics into the medium. The latter effect was most pronounced in PI 408.294A.

The importance of reduced nitrogen in soybean somatic embryogenesis was demonstrated by the comparison between MS, L2 and B5 Salts (Table 8). Embryogenesis efficiency on B5 Salts, containing 2.0 mM $NH_4^+$ was less than half that on L2 or MS Salts, which contained 12.5 and 20.6 mM $NH_4^+$ respectively. Either inorganic ($NH_4NO_3$) or organic (Gln. +Met.) reduced nitrogen supplements were able to "restore" embryogenesis efficiency in the deficient B5 medium, but the amino-nitrogen supplement appeared more effective. The observation that reduced nitrogen promotes somatic embryogenesis may be explained by a previous report that immature cotyledons have negligible nitrate reductase activity, although activity was induced by culture on nitrate-containing medium (R. C. Ackerson (1985), Crop Sci. 25:615). In other studies on soybean somatic embryogenesis, reduced nitrogen has generally been supplied as ammonium nitrate (W.D. Beversdorf et al. (1977), supra, B. Lippman, et al., (1984), supra, J. P. Ranch, et al. (1985), supra, B. J. Li, et al. (1985), supra, U. B. Barwale, et al. (1986), supra) with one exception (M. L. Christianson, et al. (1983), supra), but the data in this application indicate that under appropriate conditions, constant levels of auxin and nitrogen will promote complete embryogenesis.

In the first experiment (Table 8), the addition of casein hydrolysate (0.5 g/l) to MS medium gave an 80% increase in embryogenesis efficiency, largely by increasing mean embryo number. In the second experiment, however, all supplements (amino acids, polyamines and casein hydrolysate) depressed embryogenesis efficiency and reduced the frequency of normal embryos. These inhibitory effects of nitrogenous supplements may have resulted from the particular ammonium ion and supplement concentrations used. Studies on the effects of amino acids and ammonium on alfalfa somatic embryogenesis (D. A. Stuart and S. G. Strickland, Plant Sci. Lett., 34 (1984) 175) have demonstrated their interactions to be complex, and have shown that stimulatory or inhibitory effects may result from variation in the concentration of either factor. Several nitrogenous compounds tested here affected the appearance of embryogenesis intensity of cultures. Glutamine and casein hydrolysate produced deep green cultures, and spermidine and putrescine infrequently produced very prolific cultures. At the levels tested, however, no supplement had significant effect on somatic embryo morphology. This finding contrasts with the situation in alfalfa where several amino compounds have profound effects on somatic embryo production, morphology and "quality" (D. A. Stuart et al. (1985), supra), and in carrot which have suggested an involvement of polyamine metabolism in somatic embryogenesis (A. A. Fienberg, J. H. Choi, W. P. Lubich and A. R. Sung. Planta, 162 (1984) 532).

TABLE 8

Effects of Medium Salt Composition and Nitrogen Source on Somatic Embryogenesis. (Pooled data from two media N5 and D5), whole embryos from 10 genotypes cultured.)

| Salt Composition | Embryogenesis Frequency (A) | Mean Embryo No. (B) | Efficiency (A × B) |
|---|---|---|---|
| L2 salts | 18.1% | 1.63 ± 0.23 | 0.30 |
| MS salts | 23.8% | 1.45 ± 0.13 | 0.35 |
| MS + 0.5 g/l Casein Hydrolysate | 22.7% | 2.76 ± 0.65 | 0.63 |
| B5 salts | 8.8% | 1.33 ± 0.24 | 0.12 |
| B5 + 1.65 g/l NH$_4$NO$_3$ | 14.8% | 2.12 ± 0.71 | 0.31 |
| B5 × 1.5 g/l Met and 8.5 g/l Gln | 22.2% | 1.86 ± 0.24 | 0.41 |

TABLE 9

Effects of Amino Acids and Polyamines on Somatic Embryogenesis. (cv McCall, whole embryos cultured, N10 medium)

| Medium Supplement | Embryogenesis Frequency (A) | Mean Embryo No. (B) | Efficiency (A × B) | Frequency of Normal Embryos |
|---|---|---|---|---|
| Basal Medium | 91.9% | 4.27 ± 0.29 | 3.92 | 37.6% |
| 20 mM Glutamine | 83.1% | 3.59 ± 0.29 | 2.98 | 15.8% |
| 20 mM Methionine | 89.8% | 3.33 ± 0.28 | 2.99 | 18.9% |
| 10 mM Gln + 10 mM Met | 86.3% | 2.85 ± 0.25 | 2.45 | 22.0% |
| 20 mM Proline | 77.1% | 2.57 ± 0.22 | 1.98 | 11.4% |
| 20 mM Arginine | 74.1% | 3.05 ± 0.32 | 2.26 | 5.7% |
| 1 mM Spermine | 74.6% | 2.66 ± 0.31 | 1.98 | 2.7% |
| 1 mM Spermidine | 86.3% | 3.43 ± 0.26 | 2.96 | 18.2% |
| 1 mM Putrescine | 86.4% | 4.18 ± 0.33 | 3.61 | 23.2% |
| 0.5 g/l Casein Hydrolysate | 86.9% | 3.75 ± 0.29 | 3.26 | 15.1% |

EXAMPLE 7

Effects of Sucrose and Glucose Concentrations in Somatic Embryogenesis

Using the general procedures of Example 1, the effects of sugar concentration on somatic embryogenesis were investigated in two experiments. In the first, sucrose and glucose were compared, each at concentrations of 1.5, 3.0, 6.0 and 12.0% in N10 medium. Results are set forth in Table 10. Both McCall and J103 genotypes were tested, giving similar results. Data for J103 only are presented. In the second experiment, three concentrations of sucrose (2.5, 5.0 and 7.5%) were tested, in factorial combination with 2.5, 5.0 or 7.5 mg/l 2,4-D using PI 408.294A. Results are set forth in Table 11.

In N10 medium, embryogenesis efficiency decreased markedly as sugar concentration increased from 1.5 to 12%, (Table 10). The remaining parameters of culture response, normal embryo frequency, rooting frequency and callusing frequency all showed similar inhibition by increasing sugar concentration. Culture tissues were less dense on low-sugar media, and somatic embryos tended to appear more translucent. Sucrose and glucose gave similar results throughout, with the exception that glucose was more inhibitory to root and callus formation. In each of three 2,4-D media (D2.5, D5.0 and D7.5), embryogenesis frequency decreased as sucrose concentration increased from 2.5 to 7.5% (Table 11). There was, however, an interaction between sucrose and auxin concentration in that the optimal 2,4-D level changed from 5.0 mg/l at 2.5 and 5.0% sucrose to 7.5 mg/l at 7.5% sucrose. In this experiment, although maximum embryo production occurred with high 2,4-D and low sucrose, under these conditions a proportion of the embryos formed recallussed instead of continuing to develop.

In both NAA and 2,4-D media embryogenesis, efficiency improved as sugar concentration was decreased (Tables 10 and 11), and other parameters of culture response were similarly affected. There was little difference between sucrose and glucose as carbon sources, except that high concentrations of glucose (6 and 12%) inhibited morphogenesis more than the same sucrose concentrations. As a given weight/volume glucose concentration yields a higher osmotic pressure than the same sucrose concentration. These differences in inhibition probably resulted from the higher osmolalities of glucose media, rather than from "toxicity" effects. Most studies of soybean somatic embryogenesis have used media containing 2 or 3% sucrose (W. D. Beversdorf et al. (1977), supra, M. L. Christianson, et al. (1983), supra, J. P. Ranch, et al. (1985), supra, B. J. Li, et al. (1985), supra. U. B. Barwale, et al. (1986), supra), but in one study (B. Lippman, et al., (1984), supra) various concentrations of sucrose and glucose were tested with very low concentrations of 2,4-D. Sucrose was found to be marginally superior to glucose, and in media with 1 mg/l 2,4-D the optimal concentration for either sugar was 0.5%. A recent investigation suggests that glucose is superior to sucrose as a carbon source for immature soybean seed growth in vitro (R. C. Ackerson, Crop Sci., 25 (1985) 615.) although previous work on immature cotyledon culture had suggested that sucrose was superior (J. F. Thompson, J. T. Madison and A-M. E. Muenster., Ann. Bot., 41 (1977) 29). In the present study, an interaction between sucrose and auxin was observed, in that the optimal 2,4-D concentration increased from 5.0 mg/l to 7.5 mg/l as sucrose concentration increased from 2.5 or 5% to 7.5% (Table 11). This interaction probably explains the apparent discrepancy between the optimum 2,4-D concentration found by Lippman, et al. (1984), supra. (0.5–1.0 mg/l) and the optima found in earlier examples hereof and other work (5.0–10.0 mg/ml) Example 1 hereof and (J. P. Ranch, et al. (1985), supra, as the former study used media containing 1% sucrose while the latter studies used media with 3% sucrose.

TABLE 10

Effects of Sucrose and Glucose Concentrations on Somatic Embryogenesis (cv J103, isolated cotyledons cultured, N10 medium)

| Sugar | Embryogenesis Frequency (A) | Mean Embryo No. (B) | Efficiency (A × B) | Frequency of Normal Embryos | Rooting Frequency | Callusing Frequency |
|---|---|---|---|---|---|---|
| 1.5% Sucrose | 88.3% | 3.49 ± 0.19 | 3.08 | 49.1% | 73.3% | 46.7% |
| 3.0% Sucrose | 96.7% | 3.03 ± 0.13 | 2.93 | 13.8% | 30.0% | 45.0% |
| 6.0% Sucrose | 63.3% | 1.84 ± 0.15 | 1.17 | 2.6% | 15.0% | 10.0% |
| 12.0% Sucrose | 0 | 0 | 0 | 0 | 0 | 0 |
| 1.5% Glucose | 86.3% | 3.63 ± 0.21 | 3.13 | 50.7% | 38.8% | 20.0% |
| 6.0% Glucose | 25.0% | 1.20 ± 0.11 | 0.30 | 6.7% | 0 | 0 |
| 12.0% Glucose | 0 | 0 | 0 | 0 | 0 | 0 |

TABLE 11

Effects of Sucrose on Somatic Embryogenesis at Three 2,4-D Concentrations (PI 408.294A, whole embryos cultured).

| 2,4-D Concn. (mg/l) | Embryogenesis Frequency Sucrose Concn. (%) | | |
|---|---|---|---|
| | 2.5 | 5.0 | 7.5 |
| 2.5 | 33.3% | 16.7% | 10.7% |
| 5.0 | 53.3% | 38.2% | 3.7% |
| 7.5 | 50.0% | 28.1% | 36.7% |

EXAMPLE 8

Effects of pH on Somatic Embryogenesis

To determine the effects of medium pH on culture response, following the general procedures of Example I, a series of five N10 medium variants were prepared, with pre-culture (post-autoclaving) pH values of 5.0, 5.5, 6.0, 6.5 and 7.0 respectively (preliminary tests had shown that pre-autoclaving pH values between pH 5.5 and 7.7 would yield these post-autoclaving pH values; samples taken confirmed that the media used were within ±0.1 pH units of the desired values). In addition to the five pH-variant media listed above, three buffered media were also tested. These media each contained 10mM MES (2(n-morpholino) ethanesulfuric acid) and were adjusted to pH 5.0, 5.5 and 6.0 respectively, before autoclaving (their pH values were unchanged after autoclaving). Results are set forth in Table 12.

Varying the initial (pre-culture) pH of N10 medium between pH 5.0 and pH 7.0 had little consistent effect on embryogenesis efficiency or rooting frequency. In contrast, normal embryo production and callusing were markedly affected by the pH of the medium. Both parameters had pH optima of 5.0 or 5.5 and declined at higher pH values. In buffered media, the optimum pH for embryogenesis efficiency was 6.0 for cv. McCall and 5.5 for cv. J103, while a pH of 5.0 was inhibitory to all parameters of growth and development. In cv. McCall the frequency of normal embryos was clearly maximal in medium buffered at pH 5.5, whereas in cv. J103 normal embryo frequencies were similar at pH 5.5 and pH 5.0, although the latter value is suspect as it represents one normal embryo from a total of three produced. In all unbuffered media, the final (post-culture) pH was 6.0±0.7, whereas in buffered media the final pH was within 0.05 units of the initial value.

Other soybean somatic embryogenesis studies have used unbuffered media with pre-autoclaving pH values between pH 5.8 and 6.0, which yield post-autoclaving pH values 5.4–5.6 (W. D. Beversdorf et al. (1977), supra, M. L. Christianson, et al. (1983), supra, B. Lippman, et al., (1984), supra, J.P. Ranch, et al. (1985), supra, B. J. Li, et al. (1985), supra. U. B. Barwale, et al. (1986), supra). A pH of 6.0 was found previously to be optimal for dry weight and protein accumulation in isolated cotyledon culture (J. F. Thompson, J. T., et al. (1977), supra). In the present study, final pH was similar in media starting at different pH values and in productive and non-productive cultures. In alfalfa, somatic embryogenesis has been associated with high intracellular pH (J. Schaefer (1985) Plant Physiol. 79 (1985) 584), but no data were presented on the effects of external pH or on medium pH changes.

TABLE 12

Effects of Medium pH and Buffering on Somatic Embryogenesis (cvs McCall and J103, isolated cotyledons cultured, N10 medium).

| Medium pH | Embryogenesis Frequency (A) | Mean Embryo No. (B) | Efficiency (A × B) | [J103][1] | Frequency of Normal Embryos | [J103][1] | Rooting Frequency | Callusing Frequency |
|---|---|---|---|---|---|---|---|---|
| pH 5.0 | 93.6% | 2.41 ± 0.18 | 2.25 | [2.73] | 11.4% | [23.4%] | 27.7% | 27.7% |
| pH 5.5 | 98.0% | 2.96 ± 0.17 | 2.90 | [2.57] | 20.4% | [14.6%] | 26.0% | 28.0% |
| pH 6.0 | 98.0% | 3.02 ± 0.16 | 2.96 | [1.96] | 4.1% | [13.2%] | 20.0% | 16.0% |
| pH 6.5 | 93.9% | 3.50 ± 0.16 | 3.29 | [1.66] | 15.2% | [6.3%] | 30.6% | 18.4% |
| pH 7.0 | 94.0% | 2.80 ± 0.16 | 2.64 | [2.24] | 2.1% | [6.8%] | 28.0% | 10.0% |
| pH 5.0, 10 m M MES | 16.0% | 1.63 ± 0.32 | 0.26 | [0.10] | 6.2% | [33.3%] | 4.0% | 2.0% |
| pH 5.5, 10 m M MES | 81.3% | 2.56 ± 0.19 | 2.08 | [2.98] | 12.8% | [29.2%] | 33.3% | 37.5% |
| pH 6.0, 10 m M MES | 90.0% | 2.98 ± 0.14 | 3.88 | [2.20] | 6.7% | [2.5%] | 52.0% | 56.0% |

[1] Square brackets contain data for cv J103.
2. One normal somatic embryo of three produced.

EXAMPLE 9

Effects of Dissection of Cotyledon Tissue on Somatic Embryogenesis

To investigate the influence of the embryonic axis and the effects of various levels of tissue damage on embryogenesis, embryos were subjected to different dissection treatments before culture on N10 medium. The general procedures of Example 1 were otherwise followed. In the first experiment four treatments were compared; 1. whole embryos, 2. cotyledons damaged—two cuts were made, parallel to the long axis of the embryo, passing through both cotyledons and extending one third of the cotyledon length from the distal end, 3. axis removed—embryonic axis removed by a single cut through both cotyledons, perpendicular to the long axis of the embryo, three quarters of the way down the cotyledons from the distal end (isolated cotyledons only cultured), 4. embryo bisected—embryo bisected by a single cut through both cotyledons, perpendicular to the long axis of the embryo, half way down the cotyledons (both isolated half-cotyledons and embryo-axis portion cultured). Results are set forth in Table 13. In the second dissection experiment three levels of tissue damage, whole, halved or quartered isolated cotyledons were compared. Results are set forth in Table 14. Both McCall and J103 genotypes were used for the second experiment. Due to similar results, data for J103 only is presented. In both the first and second experiments data are presented on a "per embryo" basis.

Two experiments examined the effects of dissection treatments, using N10 medium. The first experiment (Table 13) showed that embryogenesis efficiency was increased by dissection (damage) of the embryo explant, and that both constituent parameters of efficiency were affected. It appeared that removal of the embryonic axis further increased embryogenesis efficiency ("cotyledons damaged" versus "axis removed" treatments). In the "embryo bisected" treatment, somatic embryos were formed both on isolated cotyledon portions and on cotyledon stubs attached to embryonic axes. In the second dissection experiment, "whole" isolated cotyledons were compared with cotyledons divided into halves or quarters (Table 14). Embryogenesis frequency increased as the degree of tissue damage increased, but mean embryo number was maximal in halved cotyledons, so embryogenesis efficiency was very similar in the "halved cotyledons" and "quartered cotyledons" treatments. Rooting and callusing frequencies increased with increased tissue damage. An important discrepancy between the two dissection experiments was that in the first the highest normal embryo frequency was seen with the least tissue damage ("whole embryos" treatment), whereas in the second the normal embryo frequency was highest in the treatment entailing most tissue damage "quartered cotyledons").

Damage or dissection treatments to embryo tissues definitely increased embryogenesis efficiency on N10 medium. Although the same levels of tissue damage in both treatments were not ensured, the increase in embryogenesis between the "cotyledons damaged" and "axis removed" treatments of Table 13 implies that the embryonic axis may suppress embryogenesis from cotyledon tissues. The observation that in the first experiment normal embryo frequency was highest in "whole embryo" cultures (Table 13), while in the second experiment normal embryo frequency increased with the level of tissue damage (Table 14) is difficult to interpret. It is possible that this is a genotype-specific response, as the cultivar used differed between experiments, but this question needs further investigation. The effects of dissection treatments in stimulating embryogenesis, rooting and callusing are similar to the effects of high auxin concentrations which suggests an effect of wounding on the sensitivity of cotyledon tissues to auxin. A potential mediator of such a process is ethylene. Most studies of soybean somatic embryogenesis have used a single explant type and dissection technique (W. D. Beversdorf et al. (1977), supra, M. L. Christianson, et al. (1983), supra, B. Lippman, et al., (1984), supra. B. J. Li, et al. (1985), supra, U. B. Barwale, et al. (1986), supra). One study reports embryogenesis from both whole embryos and isolated cotyledons (J. P. Ranch, et al. (1985), supra), but comparative data were not presented.

TABLE 13

Effects of Dissection on Somatic Embryogenesis I[1] (cv McCall, N10 medium).

| Dissection Treatment | Embryogenesis Frequency (A)[4] | Mean Embryo No. (B) | Efficiency (A × B) | Frequency of Normal Embryos |
|---|---|---|---|---|
| Whole Embryos | 33.9% | 1.77 ± 0.14 | 0.56 | 46.2% |
| Cotyledons damaged[2] | 83.6% | 2.75 ± 0.14 | 2.30 | 32.6% |
| Axis removed[3] | 92.4% | 3.64 ± 0.18 | 3.36 | 33.0% |
| Embryo bisected[4] | 91.6% | 3.33 ± 0.19 | 3.05 | 35.6% |

[1]All data presented on a "per embryo" basis.
[2]Two cuts, ⅓ of cotyledon length, through both cotyledons.
[3]Pair of isolated cotyledons plated.
[4]Bisected perpendicular to long axis, all parts plated.

TABLE 14

Effects of Dissection on Somatic Embryogenesis II[1] (cv J103, N10 medium).

| Dissection Treatment | Embryogenesis Frequency (A) | Mean Embryo No. (B) | Efficiency (A × B) | Frequency of Normal Embryos | Rooting Frequency | Callusing Frequency |
|---|---|---|---|---|---|---|
| Whole cotyledons | 66.7% | 1.93 ± 0.14 | 1.29 | 9.4% | 52.1% | 37.5% |
| Halved cotyledons | 76.0% | 2.68 ± 0.21 | 2.04 | 34.2% | 76.0% | 70.0% |
| Quartered cotyledons | 84.3% | 2.55 ± 0.17 | 2.14 | 38.1% | 84.0% | 100% |

[1]All data presented on a "per embryo" basis.

EXAMPLE 10

Effects of Light Intensity and Composition on Embryogenesis

To examine the influence of light intensity and composition on embryogenesis, cultures were incubated under 16 hr. photoperiods of either high (approximately 80 microEm$^{-2}$s$^{-1}$) or low (10 microEm$^{-2}$s$^{-1}$) intensity light from Grolux (Sylvania Co.) or cool white fluorescent lamps. A fifth treatment of continuous darkness was also included. Otherwise the procedures of Example 1 were used. Results are set forth in Table 15.

In the comparison of light intensities and compositions embryogenesis efficiency was higher at the low light intensity of either light type. Additionally, embryos from high light treatments were frequently bleached and subsequently showed impaired development. At both high and low light levels Grolux broad spectrum light source gave higher embryogenesis efficiencies than cool white light. Embryogenesis occurred in darkness, but at a lower efficiency than under lighted conditions. In contrast to embryogenesis, root and callus production were stimulated by high light levels.

Light intensity and composition had less influence than factors such as hormones or sugar concentration (see above). With both Grolux broad spectrum light source and cool white light a low intensity was preferable to a high intensity, while at either light level Grolux light was preferable to white light. Grolux lamps have higher emissions in the blue (430–490 nm) and red (630–680 nm) wave bands than cool white lamps (V. A. Helson Can. J. Plant Sci., 45 (1965) 461), and in previous studies have proved superior for in vitro morphogenesis (G. Schlegel and R. Schneider-Maessen. Gartenbauwissenschaft, 46 (1981) 106). In soybean zygotic embryo cultures, growth is limited in darkness and subsequent seed germination rates are reduced (R.C. Ackerson. Crop Sci., 25 (1985) 615, R. L. Obendorf, E. E. Timpo, M. C. Byrne, T. V. Toai, G. T. Rytko, F. C. Hsu and B. G. Anderson. Ann. Bot., 53 (1984) 853).

sterile clear plastic boxes (Magenta Corp., Chicago) boxes (P. A. Lazzeri, et al. (1985), supra). A number of media were tested for their ability to promote vigorous plantlet growth. Variants tested included different salt compositions; SGL (G. B. Collins and G. C. Phillips. Tissue Culture and Plant Regeneration in Trifolium pratense, in E. D. Earle and Y. Demarly (Eds.), Variability in Plants Regenerated from Tissue Culture, Praeger, N.Y., 1982, p. 26), MS (T. Murashige and F. Skoog, Physiol. Plant, 15 (1962) 473) and ½ MS (P. A. Lazzeri, et al. (1985), supra), B5 and ½ B5 (O.L. Gamborg, et al. (1968), supra), Whites[1] (modified) (P. A. Lazzeri and J. M. Dunwell. Ann. Bot., 54 (1984) 351), HPN (Hydroponic Nutrient Medium, salts (D. L. Eskew, R. M. Welch and E. A. Cary, (1983) Science 222:621) with 0.25 mg/l $NiSO_4 \cdot 6H_2O$), nitrogen source supplements; casein hydrolysate (enzymic digest, 0.5 g/l, $KNO_3$ (1.0 g/l) $NH_4NO_3$ (0.5 g/l), gelling agents; Phytoagar agar adapted for plant growth (Gibco) (6.0 g/l), Difco Bacto-agar (6.5 g/l), Gelrite gellan gum (Kelco) (2.0 g/l), growth regulators; IBA (0.05 mg/l), kinetin (0.05 mg/l), coumarin (5 mg/l), water sources; MilliQ-filtered, tap, commercial spring water (Highbridge Springs), yeast extract (Difco 1.0 g/l), Kao vitamins (modified) (K. N. Kao, Mol. Gen. Genet., 150 (1977) 225), fructose (2%), activated charcoal (1%), and buffering (10 mM MES).

The rate of somatic embryo "germination" was little affected by the differing auxin:cytokinin rations in the six NAA/BKZ media tested. A more important factor

TABLE 15

Effects of Light Intensity and Composition on Somatic Embryogenesis.
(Pooled data from 14 genotypes, whole embryos cultured, N10 medium)

| Light Treatment | Embryogenesis Frequency (A) | Mean Embryo No. (B) | Efficiency (A × B) | Rooting Frequency | Callusing Frequency |
|---|---|---|---|---|---|
| Grolux high (85 $\mu Em^{-2} s^{-1}$) | 41.8% | 1.96 ± 0.14 | 0.82 | 32.1% | 57.7% |
| Grolux low (10 $\mu Em^{-2} s^{-1}$) | 42.7% | 2.28 ± 0.14 | 0.97 | 24.0% | 37.3% |
| White high 75 $\mu Em^{-2} s^{-1}$ | 26.4% | 2.02 ± 0.16 | 0.53 | 32.5% | 50.9% |
| White low 9.5 $\mu Em^{-2} s^{-1}$ | 34.0% | 2.25 ± 0.18 | 0.77 | 26.0% | 39.3% |
| Darkness | 28.3% | 1.78 ± 0.14 | 0.50 | 22.8% | 35.9% |

EXAMPLE 11

Regeneration of Somatic Embryos to Plantlets

To facilitate growth into plants, somatic embryos formed by the procedures of Example 1 were separated from parental cultures when 2.5mm long, and were transferred to a secondary culture medium (P. A. Lazzeri, et al. (1985), supra). A number of media were tested for their ability to support embryo development and "germination." Preliminary tests indicated that low hormone levels were desirable, so the following series of media containing MS salts, B5 vitamins, 3% sucrose and combination of NAA (N) and the three cytokinins BA (B), kinetin (K) and zeatin (Z) were compared; N 0.1, BKZ 0.001; N 0.1, BKZ 0.01; N 0.001, BKZ 0.01; N 0.01, BKZ 0.1; N 0.001, BKZ 0.1 and N 0.1, BKZ 0.01, GA30.1 (all hormone concentrations in mg/l, at each BKZ level the individual cytokinins were each at one third of the total cytokinin concentration). This media series gave a range of auxin:cytokinin ratios between 100:1 and 1:100.

For the production of rooted plantlets suitable for transfer to soil, "germinated" embryos (with outgrowth of the primary leaves) were transferred to Magenta was the intrinsic "maturity" of the somatic embryo; those embryos with visible, well-defined apices would "germinate" rapidly on any of the six media, while those lacking a defined shoot apex would generally exhibit a lag period of 20–60d before "germinating." From assessments of the general "health" of cultures, a medium containing 0.05 mg/l NAA and 0.1 mg/l BKZ (P. A. Lazzeri, et al. (1985), supra) was adopted for routine use.

Although "germinated" somatic embryos with emerged primary leaves rooted readily, produced trifoliates, and grew in size when transferred to low-salt media in Magenta sterile clear plastic boxes, older leaves often displayed interveinal chlorosis and in some cases premature leaf senescence. This chlorosis did not prevent efficient transfer to soil. (The chlorosis/senescence response was not confined to somatic embryo-derived plantlets, but was also seen in seedlings.) A large number of media variants were surveyed in attempts to improve plantlet quality.

Factors which affected plantlet growth were salt composition, water source, gelling agent and yeast extract. A medium containing HPN salts and 0.25 g/l yeast extract, dissolved in tap water, adjusted to pH 5.9 before autoclaving and gelled with 0.65 g/l Difco Bacto-agar gave good growth. This HPN medium was supplemented with either 5 mg/l coumarin or 0.005 mg/l IBA for genotypes which did not root readily.

The frequency and rate of somatic embryo "germination" was closely correlated with embryo "normality"; abnormal embryos had lower "germination" rates and longer lag periods before shoot outgrowth. Similar correlations have been reported in alfalfa (D. A. Stuart, et al. (1984), supra). In contrast to the situation in alfalfa, and in other soybean work (J.P. Ranch, et al. (1985), supra), in the current study neither amino acid additions to induction media, nor hormone manipulations in germination media had consistent effects on embryo germination.

Leaf chlorosis and premature leaf senescence in regenerated plantlets was peculiar to in vitro conditions; the observation that chlorotic leaves would re-green in plantlets transferred to soil implied toxicity or deficiency in culture. Use of the modified HPN medium, based on a salt composition developed for hydroponic culture (D. L. Eskew, et al. (1983), supra) instead of a salt composition developed for the growth of tissues in vitro significantly improved plant health. Difficulty in growing satisfactory soybean plantlets in vitro has rarely been discussed elsewhere (Z. Yang, Z. Chan, Z. Liv, and Z. Ahang, Bulletin of Sciences, 16 (1984) 1012), but reports of problems in rooting regenerants and in establishing them in soil (B. Lippman, et al., (1984), supra, U. B. Barwale, et al. (1986), supra, M. L. Christianson, et al. (1983), supra) suggest that plantlet growth conditions are frequently sub-optimal.

EXAMPLE 12

Regeneration of Plantlets to Whole Plants

Plantlets of Example 11 with developed primary leaves were transferred to one-half MS 2S medium ($\times \frac{1}{2}$ MS macro salts, $\times 1$ micro salts, B5 vitamins, 2% sucrose, 0.65% Phytoagar agar adapted for plant growth) supplemented with 0.005 mg/l IBA, and dispensed into Magenta sterile clear plastic boxes.

Boxes were placed under a 16 hour photoperiod of intensity 50-100 microEm$^{-2}$s$^{-1}$ (500-1000 lux) from Grolux broad spectrum light source or cool-white fluorescent lamps.

When plantlets with well-developed root systems were observed, they were transferred to pots containing sterilized (autoclaved or microwaved) potting mix (2:2:1 soil:Promix horticultured soil mix:sand sand mix). Plants were fed weekly with Peters complete liquid fertilizer 20:20:20 complete plant food. Plants were kept covered to reduce transpiration during the hardening period. Mite infestations and whiteflies were controlled by means known to the art. See P. A. Lazzeri, et al (1985) supra.

Whole plants bearing seed were regenerated.

EXAMPLE 13

Synergistic Effect of Low Carbohydrate/Low Auxin Levels on Somatic Embryogenesis Although prior examples showed optimal concentrations of 2,4-D to be between 5 and 10 mg/l, and of NAA to be at least 30 mg/l, the effects of reduced auxin concentrations were tested at varying sugar concentrations. Otherwise the procedures of Example 1 were followed. Results are set forth in Table 16.

Total somatic embryogenesis efficiency is shown to be optimal throughout at 1% or 2% sucrose. The frequency of normal embryos is optimal at the lowest sucrose concentration (0.5%). The efficiency of normal embryo production (frequency of normal embryos $\times$ mean normal embryo number) is optimal at 1% sucrose. The sucrose concentration also affects the number of cotyledons formed on somatic embryos. The most normal, dicotyledonous embryos are, at each auxin concentration, produced by 0.5 sucrose. At each auxin concentration (6.25, 12.5, 25 or 50 mg/l) the frequency of normal (dicotyledonous) embryos decreases as sucrose concentration increases. With the use of low sucrose concentrations, high levels of efficiency and embryo normality are obtained with relatively low auxin concentrations (6.25 mg/l NAA).

As shown in Table 16, the productivity of cultures during a second period of incubation on a 6.25 NAA, 2.0% sucrose medium is increased by having a low sucrose (0.5%) concentration in the primary culture medium.

Also, as shown in Table 16, germination of somatic embryos (column headed "% P.LVS"$\leqq$5 mm" (percent primary leaves $\leqq$5 mm)) is best among embryos produced on 1% or 2% sucrose.

TABLE 16

| Somatic Embryogenesis and Germination Efficiency Using Lowered Sugar and Auxin Concentrations | | | | | | | |
|---|---|---|---|---|---|---|---|
| NAA Concn. mg/l | Sucrose Concn. mg/l | Efficiency Normal Embryos | Frequency Normal Embryos (%) | Efficiency (Total) | Frequency of Normal Cotyledons (2) | Productivity During Second Period of Incubation | % P.LVS .05 mm |
| 6.25 | 0.5 | 1.04 | 76.5 | 1.70 | 58 | 0.42 | 13.6 ± 2.4 |
|  | 1.0 | 1.82 | 69.3 | 3.95 | 42 | 0.29 | 16.4 ± 2.1 |
|  | 2.0 | 1.72 | 69.0 | 4.18 | 22 | 0.19 | 17.2 ± 2.9 |
|  | 4.0 | 0.07 | 16.7 | 0.64 | 13 | 0.06 | 9.0 ± 0.0 |
| 12.5 | 0.5 | 0.82 | 87.0 | 1.28 | 45 | 0.54 | 15.3 ± 3.0 |
|  | 1.0 | 1.02 | 57.0 | 2.78 | 42 | 0.21 | 2.5 ± 3.4 |
|  | 2.0 | 1.58 | 55.2 | 4.48 | 22 | 0.25 | 23.0 ± 2.2 |
|  | 4.0 | 0.09 | 14.9 | 0.82 | 13 | 0.05 | 0 |
| 25 | 0.5 | 0.37 | 67.7 | 0.65 | 68 | 0.69 | 15.5 ± 11.8 |
|  | 1.0 | 0.95 | 72.1 | 3.28 | 50 | 0.21 | 18.1 ± 3.6 |
|  | 2.0 | 0.88 | 52.8 | 3.56 | 27 | 0.31 | 19.9 ± 3.1 |
|  | 4.0 | 0.08 | 13.1 | 1.24 | 25 | 0.08 | 37.0 ± 0.0 |
| 50 | 0.5 | 0.42 | 81.3 | 0.60 | 81 | 0.48 | 4.2 ± 2.6 |
|  | 1.0 | 0.77 | 65.0 | 1.52 | 50 | 0.34 | 8.3 ± 2.6 |
|  | 2.0 | 0.79 | 55.6 | 2.25 | 35 | 0.30 | 23.0 ± 2.6 |
|  | 4.0 | 0.40 | 25.6 | 2.52 | 31 | 0.17 | 13.5 ± 7.0 |

EXAMPLE 14

Transformation of *Glycine clandestina*

*Agrobacterium tumefaciens* containing the vector pH575 were prepared. The construction of this vector is more fully described in EPO Publication No. EP 223,417 published May 27, 1987. This vector carries kanamycin resistance and octopine synthase genes. The bacteria were cultured on a plate of YEP medium (10.0 g/l yeast extract, 10.0 g/l peptone, 5.0 g/l NaCl, 15 g/l agar, pH7.0) containing kanamycin, at 28 degrees C. Some of the Agrobacterium colonies were scraped off and resuspended in YEP broth or minimal medium. About 25 to 50 colonies were suspended per 1.5 ml of medium. The suspension colonies were allowed to grow overnight.

*G. clandestina* plants were grown in a greenhouse to flowering. The plants were grown one to two plants per 25 cm diameter pot in a sterilized 2:2:1 soil:Promix horticultural soil mix:sand sand mix and fed weekly with Peters liquid fertilizer 20:20 20 complete plant food. During short days natural light was supplemented with 13 hours of artificial (high pressure sodium) light. Mite infestations were controlled with Plictran, a trademark of Dow Chemical Co., or Pentac, a trademark of Zoecon Co. Whiteflies were controlled with Orthene, a trademark of Chevron Corp., and powdery mildew with Benelate, a trademark of Dupont.

Leaf sections were taken from immature leaves of the plants and transferred to a dish of cold water to keep the tissues from desiccating. The explants were washed and sterilized with 70% isopropanol for one minute and 10% Chlorox with a drop of Liquinox for 10-15 minutes, then twice rinsed with sterile water for five minutes.

The plant tissue was plated onto a regeneration medium containing cytokinins, using 20-30 pieces of plant material per plate, and preincubated for 1 to 2 days.

The overnight suspension cultures of Agrobacterium were streaked out onto YEP medium containing kanamycin to give single colonies. A single colony was chosen and used to inoculate 25 ml of YEP broth containing kanamycin. The culture was grown overnight at 28 degrees C. in a shaking water bath. The culture was spun down to harvest the cells which were resuspended in YEP broth or minimal medium.

After pre-incubation, each piece of tissue was inoculated with 0.5 to 1.0 µl of the resuspended overnight culture containing about 106 organisms per ml. Prior experiments showed that when tissue was dipped in the culture solution, Agrobacteria overgrew and killed the tissue. The material was allowed to grow in the presence of the Agrobacteria for two days and then transferred to the regeneration medium containing Mefoxin at a concentration of 300 to 400 µg per ml.

After two to seven days, the material was transferred to a regeneration medium containing kanamycin at a level of 100 to 300 µg/ml and Mefoxin to allow selection for transformed tissue.

The material was then subcultured on the regeneration media containing antibiotics biweekly until shoots were formed. The plantlets with shoots were then transferred directly to a rooting medium. Rooted plants were regenerated.

EXAMPLE 15

Transformation of *Glycine max*

*Agrobacterium tumefaciens* containing the vector pH 4-1 (EPO Publication No. EP 223,417, published May 27, 1987), having a kanamycin resistance marker gene and an octopine synthase gene, were cultured as described in Example 14.

*Glycine max* plants were grown as described in Example 14. The tissue used for transformation was immature cotyledon tissue from 3-5 mm immature seeds. The pods were removed from the plants and stored in cold water, then rinsed under cold water to wash off dust or dirt and help cut down on fungus infections later. Seeds of approximately 3-5 mm in length were preselected by holding pods up against the light. The pods were sterilized in 70% isopropanol for one minute, 25% Chlorox plus a drop of Liquinox for 10-15 minutes, then twice rinsed in sterile water for five minutes each. The immature seeds were excised from the pods and the embryonic axes removed by making a cut through both cotyledons distal to the shoot apex region. Pressure was applied on the opposite end of the embryo until the cotyledons emerged.

The cotyledon pairs were plated onto regeneration media at a rate of 10 per 100 mm dish (30 mls of medium per dish), and preincubated for two days.

The regeneration media used were embryogenesis media as follows: (1) MS salts, B5 vitamins, 3% sucrose, 500 mg/l glutamine, 100 mg/l methionine, 10 mg/l NAA, 0.6% Phytogar agar adapted for plant growth, pH 5.9 (before autoclaving); and (2) MS salts, B5 vitamins, 3% sucrose, 500 mg/l glutamine, 100 mg/l methionine, 10 mg/l 2,4-D, 0.6% Phytoagar agar adapted for plant growth.

The preincubated tissue was inoculated with 0.5 µl of resuspended Agrobacteria. It was critical not to add too much Agrobacteria because it would quickly overgrow the tissue and kill it. The Agrobacteria suspension used for inoculation contained about $10^6$ organisms per ml. The cotyledons were allowed to grow in the presence of the bacteria for two days and then were transferred to fresh embryogenesis media containing antibiotics to kill off the Agrobacteria (200 mg/ml Mefoxin or Claforan) and 100 µg/ml kanamycin to select for transformed somatic embryos.

The cotyledons were subcultured every 28 days back onto embryogenesis medium plus antibiotics and kanamycin until somatic embryos were formed.

The shoot multiplication and rooting media used were as described in Example 14. The procedures of Example 14 and P. Lazzeri, et al. (1985), supra, were followed to obtain a regenerated plant which had been transformed with Agrobacteria containing pH 4-1.

The plant was transferred to the potting soil mix of Example 12 and allowed to grow until leaf tissue could be spared for testing purposes. Tissue was tested for kanamycin resistance by performing a recallusing assay in the presence of 50 and 100 µg/ml kanamycin, and for octopine synthesis by paper electrophoresis. The tissues grew in the presence of kanamycin and appeared to be positive for the presence of octopine.

The plant continued to grow, appeared normal, and produced multiple seed pods.

EXAMPLE 16

Genotype Screen for Embryogenic Potential

A genotype screen was conducted to determine embryogenic potential and susceptibility of various soybean genotypes to *Agrobacterium tumefaciens* strain A281, also known as EHA101, and described in E. Hood, et al. (1986) J. Bact. 168:1291-1301. This strain is available from the authors upon request. The medium used for this screen consisted of MS salts with B5 vitamins, 1.5% sucrose, 10 mg/l NAA and 0.2% Gelrite gellan gum. Cotyledons were taken from immature embryos between 3 and 5 mm in length, and the embryonic axes removed. Cotyledons were placed abaxial side up on the medium. Results are set forth in Table 17. "Percent response" refers to the number of plated cotyledons that gave somatic embryos. "Mean" under the column heading "Responding basis" refers to the number of somatic embryos produced by cotyledons that responded by forming somatic embryos. "Mean" under the heading "Overall Basis" refers to the number of somatic embryos formed per plated cotyledon. "N" refers to the number of cotyledons evaluated for regeneration. Agrobacterium susceptibility was determined by gall formation.

Several excellent regeneration genotypes were found, including two that regenerate significantly better than the previous standard, J103. These genotypes are "Manchu" and "Williams". A few of the genotypes whose immature cotyledons produce galls after co-cultivation with Agrobacterium were also identified. The best genotypes were "McCall", J103, Williams and "Peking", in that order.

0.65% agar) containing N10.00 or D25.00 or D0.50 (NAA or 2,4-D and mg/l) from zygotic embryos of cultivar McCall cultured on N10 medium were fixed at one or at two day intervals in 3% gluteralde in phosphate buffer pH 6.8 or FAA (formaldehyde:acetic acid:alcohol) (M. E. McCulley et al. (1981) "The Study of Plant Structure, Principles and Selected Methods", Melbourne, Australia, 6.58-6.92).

Fixed embryos were dehydrated through a TBA series to paraffin oil and embedded in Tissue Prep (Sigma Co., St. Louis). Sections were cut on a rotary microtome 8-10 μm in thickness. Slides were stained in hematoxylin (J. E. Sass (1958) *Botanical Microtechnique*), safranin, toluidine blue (M. E. McCulley et al. (1981) supra), nile red, aniline blue (J. E. Sass (1958) supra), iodine (W. A. Jensen (1962) *Botanical Histochemistry*), periodic-acid-Schiff's reagent (J. E. Sass (1958) supra), as appropriate.

Soybean somatic embryos can have both single and multicellular origins. The embryogenic pathway from globular to torpedo stage resembles that of zygotic embryogenesis. As the somatic embryos continue to form on media containing NAA, the hypocotyl, especially the basal region, elongates more than that of zygotic embryos and the apex can be reduced or absent. The cotyledons are most often correctly initiated but are often reduced in size. When 2,4-D is used as an auxin source, the most pronounced abnormality is incorrect cotyledon initiation causing somatic embryos to appear horn-shaped. Generally, the apical region is depressed or absent.

Differences in initiation patterns between the two auxin treatments were observed. Although indirect and

TABLE 17

| | | RESPONDING BASIS | | OVERALL BASIS | | | |
|---|---|---|---|---|---|---|---|
| GENOTYPE | % RESPONSE | MEAN | STANDARD ERROR | MEAN | STANDARD ERROR | N | Agro. Suscep.: |
| 1 Manchu | 66.49 | 3.14 | 0.16 | 2.09 | 0.15 | 188 | − |
| 2 Williams 82 | 65.81 | 1.95 | 0.10 | 1.28 | 0.10 | 155 | + |
| 3 J103 | 56.50 | 2.04 | 0.11 | 1.16 | 0.10 | 200 | + |
| 4 Clark r | 45.30 | 2.47 | 0.14 | 1.12 | 0.10 | 298 | − |
| 5 P.I. 283332 | 44.67 | 2.22 | 0.17 | 0.99 | 0.12 | 150 | − |
| 6 Harosoy | 42.00 | 2.24 | 0.44 | 0.94 | 0.21 | 100 | − |
| 7 McCall | 39.07 | 2.00 | 0.17 | 0.78 | 0.10 | 151 | + |
| 8 Forrest | 36.97 | 1.60 | 0.10 | 0.59 | 0.06 | 238 | − |
| 9 Douglas | 32.50 | 1.51 | 0.11 | 0.49 | 0.06 | 200 | − |
| 10 Kent | 31.12 | 1.49 | 0.14 | 0.46 | 0.07 | 196 | + |
| 11 Heilungjiang 26 | 25.91 | 1.65 | 0.13 | 0.43 | 0.06 | 220 | + |
| 12 Elf | 28.65 | 1.45 | 0.12 | 0.42 | 0.06 | 171 | − |
| 13 Essex | 22.62 | 1.66 | 0.15 | 0.38 | 0.06 | 168 | − |
| 14 Stafford | 22.54 | 1.67 | 0.11 | 0.38 | 0.06 | 173 | − |
| 15 Ripley | 22.73 | 1.63 | 0.18 | 0.37 | 0.07 | 132 | − |
| 16 Heilungjiang 10 | 27.50 | 1.29 | 0.08 | 0.36 | 0.05 | 200 | − |
| 17 Peking | 16.50 | 1.76 | 0.21 | 0.30 | 0.06 | 200 | + |
| 18 Manitoba Brown | 19.57 | 1.33 | 0.12 | 0.26 | 0.05 | 138 | − |
| 19 Pennyrile | 11.43 | 1.69 | 0.25 | 0.19 | 0.54 | 140 | + |
| 20 P.I. 423897 | 9.29 | 1.85 | 0.34 | 0.17 | 0.06 | 140 | + |
| 21 P.I. 420338 | 12.50 | 1.33 | 0.13 | 0.17 | 0.04 | 120 | − |
| 22 Sooty | 15.79 | 1.00 | 0.00 | 0.16 | 0.04 | 76 | − |
| 23 Shiro | 6.96 | 1.50 | 0.50 | 0.10 | 0.05 | 115 | − |
| 24 Lee | 5.00 | 1.50 | 0.50 | 0.08 | 0.04 | 160 | + |
| 25 Cobb | 2.15 | 1.25 | 0.25 | 0.03 | 0.01 | 186 | + |

LSD (.05) = 0.89

EXAMPLE 17

Identification of Particularly Embryogenic Regions

Histological evaluations were conducted on somatic embryo initiation and development following induction on NAA or 2,4-D.

Zygotic embryos of the cultivar J103 were cultured on medium (MS salts B5 vitamins 1.5% sucrose and direct somatic embryogenesis was observed for both auxins, there were differences in the way direct somatic embryos were initiated. 2,4-D caused the epidermis and several adjacent sublayers of cells to form a meristematic zone. Embryos initiated along this zone were characterized as having a broad suspensor region indicative of multicellular initiation (E. G. Williams et al.

(1986) Annal. Bot. 57:443-462). NAA embryos were more often initiated from cells which were surrounded by a thick cell wall from neighboring cells especially neighboring cells which were dying. Narrow suspensors indicative of a single-cellular initiation were observed.

For either auxin treatment, cotyledon-stage somatic embryos were associated with a zone of collapsed cells, cells which may have served as a source of nutrients for the developing embryos or may have caused an isolation of certain cells allowing them to enter an embryogenic pathway.

The formation of cells exhibiting characteristics of embryogenic tissues, namely small cell size, dark-staining cytoplasm, a large dark-staining nucleus with distinct nucleoli and numerous starch grains were observed for both auxin treatments. Embryogenic cells exhibited distinct cell walls between neighboring cells. Embryos forming from such tissues had narrow suspensors. Some cells within these tissues were multinucleate, with three differently sized nuclei and greatly increased cell size not unlike cells during megametogenesis.

Additionally, different areas of the explant cotyledons gave rise to somatic embryos. On media containing NAA, embryos were initiated along the periphery of the uncut portion of the explanted cotyledons. This "fertile crescent" region is shown in FIG. 1. Here the greatest number of somatic embryos with normal morphology were initiated on cotyledons placed with their abaxial surface to the medium. When placed on 2,4-D amended medium, explanted cotyledons placed abaxial-surface to the medium were initiated from the central adaxial region of the explanted cotyledon. This orientation appeared to inhibit embryogenesis from the "fertile crescent" region. This "fertile oval" region is shown in FIG. 1. With 2,4-D, the cotyledons placed adaxial side to the medium gave the greater number of normal embryos, and the initiation was from the periphery "fertile crescent" region rather than the central adaxial region. 2,4-D produced a greater total number of embryos. The number of normal embryos produced by the auxin treatments did not appear to be different in this study. However, when examining the auxin-by-orientation interaction, 2,4-D with the adaxial side to the medium produced more normal embryos than NAA with the abaxial side to the medium. Table 18 shows the effects of media and orientation in embryogenesis.

TABLE 18

| Effects of Media and Orientation on Embryogenesis | | | |
|---|---|---|---|
|  |  | Mean | Standard Error |
| Total Embryos | D25 | 8.42 | 1.588 |
|  | N10 | 1.92 | 0.199 |
| Abaxial | D25 | 11.13 | 0.989 |
|  | N10 | 2.08 | 0.119 |
|  | Combined | 4.77 | 0.364 |
| Adaxial | D25 | 5.70 | 0.855 |
|  | N10 | 1.76 | 0.122 |
|  | Combined | 2.98 | 0.291 |
| Normal Embryos | D25 | 1.22 | 0.580 |
|  | N10 | 0.35 | 0.074 |
| Abnormal Embryos | D25 | 7.19 | 1.334 |
|  | N10 | 1.56 | 0.186 |
| Abaxial-normal | D25 | 0.52 | 0.133 |
|  | N10 | 0.65 | 0.072 |
|  | Combined | 0.63 |  |
| Adaxial-normal | D25 | 1.93 | 0.557 |
|  | N10 | 0.04 | 0.032 |
|  | Combined | 0.61 |  |
| Abaxial-abnormal | D25 | 10.61 | 0.949 |
|  | N10 | 1.43 | 0.100 |

TABLE 18-continued

| Effects of Media and Orientation on Embryogenesis | | | |
|---|---|---|---|
|  |  | Mean | Standard Error |
|  | Combined | 4.16 |  |
| Adaxial-abnormal | D25 | 3.75 | 0.679 |
|  | N10 | 1.72 | 0.119 |
|  | Combined | 2.34 |  |

EXAMPLE 18

Maceration

Maceration of the immature cotyledons by crushing them on sterile No. 35 mesh (500 μm) has provided a means to wound those regions of the cotyledon with embryogenic potential. Twenty cotyledons were macerated on each 2 cm² piece of mesh to produce ¼ mm² pieces. If the tissue is left on the mesh, the mesh itself becomes a convenient way to easily and efficiently transfer large numbers of cotyledons from one medium to another during the transformation/regeneration process.

Stainless steel mesh produced a significantly higher frequency of embryogenesis than did nylon mesh. Steel has the advantage that it is easy to sterilize and is reusable. Bronze mesh produced no results and is toxic to all tissues. Genotypes with medium to poor regeneration capacity (e.g. McCall, Peking, or "Manitoba Brown") respond especially well to maceration on stainless steel mesh. Macerated cotyledons of these genotypes actually produce more somatic embryos than non-macerated cotyledons (see Table 19). Running a weak electric current (2 μA) through the steel mesh led to a further increase in the frequency of embryogenesis.

TABLE 19

| Effect of Nylon vs. Stainless Steel Mesh on Embryogenesis | | | |
|---|---|---|---|
| Genotype | Embryos/20 Cotyledons | | % Improvement |
| Improvement | Nylon | Steel | Steel/Nylon |
| J103 | 5.00 | 5.40 | 0.84 |
| Manchu | 0.50 | 18.10 | 0.004 |
| McCall | 0.22 | 12.40 | 0.02 |
| Williams | 2.50 | 2.00 | 0.73 |
| Heilongjiang 10 | 1.83 | 7.75 | 0.12 |
| Douglas | 0.70 | 2.50 | 0.092 |

EXAMPLE 19

Transformation and Regeneration of Transformed Plant

Plants of Peking were grown in the greenhouse. Pods were surface sterilized and immature cotyledons 3-5 mm in length excised (P. A. Lazzeri et al. (1985) supra) after removing the embryonic axis. Not all cells of the immature cotyledons are capable of forming somatic embryos. Cells with embryogenic potential following exposure to NAA are limited to a narrow crescent near the distal perimeter of the immature cotyledons as described in Example 17. Cells in this region form somatic embryos via direct embryogenesis, that is, there is no intervening callus phase. To wound this region and permit direct contact between the Agrobacterium and the cells with embryogenic potential, the immature cotyledons were pressed against a 500 μm mesh and placed on media containing MS salts, B5 vitamins, 1.5% sucrose, 10 mg/l NAA, and 0.2% Gelrite gellan gum as a solidifying agent. The macerated cotyledons were inoculated with an overnight suspension of LBA4404 (pH5PZ3D). PH5PZ3D is a micro Ti plasmid that contains the 15 kd zein coding region behind the β-phaseolin promoter. This plasmid also contains the neomycin phosphotransferase II gene that can be used as a selectable marker. Following overnight incubation at 28° C. the tissue was transferred to the above media supplemented with 500 mg/l of Mefoxin (cefoxitin). Somatic embryos were removed at 30 days and placed on media as described above, except that the growth regulators were changed to 0.17 mg/l each of benzyladenine, kinetin, and zeatin, and 0.05 mg/l of NAA. Embryos were transferred on this medium at monthly intervals until germination occurred. Germinating embryos were transferred to media with HPN salts solidified with 0.15% Gelrite gellan gum. Rooted plants were transferred to soil and allowed to grow normally in a greenhouse. A plant that has now grown to maturity displayed no morphological abnormalities and had normal seed set.

DNA was extracted from leaf tissue collected near the top of the mature plant and digested with EcoRI. Southern hybridizations were made using a 4.7 kb EcoRI fragment of pH5PZ3D that contained the phaseolin/zein construct. The EcoRI fragment hybridized with a 2.7 kb band from the transformed soybean. No hybridization was shown in untransformed soybean DNA used as a control. Octopine production tested negative.

EXAMPLE 20

Transformation

The following more fully describes the transformation protocol used in the above Example resulting in the transformed regenerated plant recovered to date. About 5000 immature cotyledons 3–5 mm in length were dissected out of surface-sterilized pods and places, abaxial side down, on stainless steel or nylon mesh, on which they were then crushed. The mesh was then placed on N10 medium (MS salts, B5 vitamins, 10 mg/l of α-NAA, 1.5% sucrose and 0.2% gellan gum). Each mesh square with 20 macerated cotyledons was inoculated with 50 µl of an overnight suspension culture of Agrobacterium strain EHA101 (the disarmed version A281) carrying pH5PZ3D. Co-cultivation of the macerated tissue with Agrobacterium took place overnight at 28° C.

The following day, the cultures were transferred to N10 medium supplemented with G418 at 1 mg/l and Cefoxitin at 500 mg/l. After one month, resulting somatic embryos were transferred to BKZN medium (MS salts, B5 vitamins, 6-BA, kinetin, and zeatin, each at 0.017 mg/l α-NAA at 0.05 mg/l, 2% sucrose, and 0.2% Gelrite gellan gum supplemented with 500 mg/l of Cefoxitin for further growth and development of the somatic embryos. Embryos were maintained on BKZN medium, being transferred at monthly intervals, until germination occurred, at which time they were transferred to media with HPN- salts.

EXAMPLE 21

Time of Inoculation

To determine the best time to add Agrobacteria after explanting the cotyledons, cotyledons (100 per treatment) were explanted onto MS medium containing 1.5 sucrose, inoculated at the times indicated in Table 20 by placing 1 µg of an overnight suspension of Agrobacteria thereon, and after two days' co-cultivation, placed on the same medium containing 500 mg/l Mefoxin. Results are shown in Table 20. Callus were rated on a 0–5 scale where 0= no callus, 1= identifiable callus, and 5= large callus.

TABLE 20

| GENOTYPE Time of inoculation | McCall % cotyledons callusing | callus rating | J103 % cotyledons callusing | callus rating |
|---|---|---|---|---|
| 0 days | 53% | 1.65 ± .08 | 75.55% | 2.30 ± .09 |
| 1 day | 45.56% | 1.82 ± .12 | | |
| 2 days | 0* | — | 45.56% | 1.85 ± .13 |

* Result of 2 independent trials

It appears that best results are obtained by adding the Agrobacterium at the time the cotyledons are explanted. J103 appears to be more susceptible to Agrobacterium than McCall. Callus forming on the cotyledons was removed and placed on hormone-free MS medium, supplemented with .5 g/l cas-amino acids (MS-CAS medium).

EXAMPLE 22

Co-Cultivation Time

To determine whether the 3-day exposure time to Agrobacteria used by Owens and Cress (1985) Plant Physiol. 77:87–94 gives better results than a shorter exposure time, 100 embryos each of McCall and J103 genotypes were inoculated with Agrobacterium A281 immediately after explanting. After co-cultivation for 1 and 3 days, frequencies of response were compared results were as follows:

McCall at 1 day: 52.78 of the cotyledons responded with a mean callus rating of 1.05±023. Three continued to go on hormone-free media.

J103 at 3-day co-cultivation period: 13.89 of the cotyledons responded, with an average callus rating of 2.28 ±0.24.

McCall at 3-day co-cultivation: 46 "galls" appeared on the cotyledons. These failed to grow on hormone-free media, so they were probably not galls to begin with. The results of this treatment must be 0 galls obtained.

One-day co-cultivation appears best. Tissue death begins to increase with increasing exposure to Agrobacterium, even though J103 and McCall do not appear to be as susceptible (i.e., sensitive to tissue damage) as other genotypes such as Peking and Century.

EXAMPLE 23

Selection Agents

Experiments were performed to determine optimum levels of the selection agents G418 and kanamycin, and use of agar and gellan gum.

Data from previous experiments has shown that 25 mg/l G418 might be too high. Embryo formation responses were compared using the two different section agents in varying concentrations on different media. Response also included root (usually blind) formations. Results were as follows:

K50+agar—0.10 embryos responded. Greenish-yellow in color.

K50+gellan gum—5/10 embryos responded. Greenish-yellow to green in color.

K100+agar—1/10 embryos responded. Greenish-yellow in color.

K100+gellan gum—3/10 embryos responded. Whitish-yellow to light green in color.

K200+agar—0/10 embryos responded. Yellowish-green color.
K200+gellan gum—0/10 embryos responded. Whitish-yellow to yellow-green color.
K300+agar—0/10 embryos responded. Yellow-green color
K300+gellan gum—0/10 embryos responded. Yellow-white color
G10+agar—0/5 embryos responding. 4/5 normal green color, 1/5 white.
G10+gellan gum—0/5 embryos responding. 4/5 normal green color, 1/5 white.
G15+agar—0/10 embryos responding. All have normal green color.
G15+gellan gum—0/10 embryos responding. 9/10 have normal green color, 1/10 white.
G20 +agar—1/10 embryos responding. Yellowish-green color
G20+gellan gum—0/10 embryos responding. 9/10 yellowish-green color, 1/10 white.
G25+agar—0/10 embryos responding. 5/10 green, 5/10 yellow-green.
G25+gellan gum—0/10 embryos responding. 7/10 yellow-green, 3/10 white.
*G418 appeared very unevenly spread.

G418 produced more uniform results than kanamycin between agar and gellan gum. Kanamycin gave better results on agar than on gellan gum. Levels of G10 or K50 on agar should be sufficient to act as a screen for transformed tissues.

EXAMPLE 24

Antibiotics and Selection

*Agrobacterium tumefaciens* strains EHAI01 (A281) and LBA4404 containing the vector pH5PZ3D were prepared. This vector carries kanamycin resistance and octopine synthase genes. The bacteria was cultured on a plate of LB medium (5.0 g/l yeast extract, 10.0 g/l tryptone, 5.0 g/l NaCl, 15 g/l agar, pH 7.5) at 28° C. Some of the Agrobacterium colonies were scraped off and resuspended in LB broth. The suspension colonies were allowed to grow overnight at 28° C. Antibiotics used in the medium for LBA4404 (pH5PZ3D) were streptomycin 250 mg/l; kanamycin 25 mg/l; and tetracycline 2.8 mg/l; and antibiotics used for EHA101 (pH5PZ3D) were kanamycin 50 mg/l; nalidixic acid 20 mg/l; and tetracycline 2 mg/l.

Embryos generated from tissue of several genotypes, with and without selection were evaluated after cocultivation with the Agrobacteria containing pH5PZ3D. One hundred cotyledon pairs were used for each treatment. Ten cotyledon pairs were macerated per nylon mesh square. All bacteria used contained pH5Z3D. Co-cultivation periods were 1 day only. Results are set forth in Table 21.

TABLE 21

| Treatment | Genotype | Bacteria | Initiation Media Supplements | # Somatic Embryos |
|---|---|---|---|---|
| a | J103 | LBA4404 | mefoxin, 50 μg/ml | 1 |
| b | J103 | EHA101 | mefoxin 500 μg/ml | 29 |
| c | J103 | LBA4404 | mefoxin 500 μg/ml; G418 10 μg/ml | 0 |
| d | J103 | EHA101 | mefoxin 500 μg/ml; G418 10 μg/ml | 36 |
| e* | Peking | LBA4404 | mefoxin 500 μg/ml | 10 |
| f | Peking | EHA101 | mefoxin 500 μg/ml | 0 |
| g | Peking | LBA4404 | mefoxin 500 μg/ml; | 0 |

TABLE 21-continued

| Treatment | Genotype | Bacteria | Initiation Media Supplements | # Somatic Embryos |
|---|---|---|---|---|
| h | Peking | EHA101 | G418 10 μg/ml mefoxin 500 μg/ml; G418 10 μg/ml | 0 |

*Described in Example 19

The number of somatic embryos obtained from each treatment are presented in the final column of the above table. LBA4404 appears to be more effective on Peking, while EHA101 appears to be best for J103.

One of the purposes of this experiment was to determine whether it was necessary or advisable to start selection following the co-cultivation period. Initial results suggest that embryos (partially transformed) will still develop under selection in J103, but not Peking. In either case, the number of embryos obtained is very small, and one need not worry about being overwhelmed with embryos. Transformed embryos may be obtained even in the absence of selection.

We claim:

1. A method for the somatic embryogenesis of a plant of *Glycine max* comprising:
   (a) excising cotyledon tissue from immature embryos of said plant;
   (b) culturing said cotyledon tissue on an induction medium comprising an auxin of the NAA family at a concentration of between about 15 mg/l and about 50 mg/l.

2. The method of claim 1 in which the auxin concentration is at least about 30 mg/l.

3. The method of claim 2 in which the auxin comprises NAA.

4. The method of claim 1 wherein an embryo of step (b) is further cultured on a shooting medium until a plantlet is generated therefrom.

5. The method of claim 4 wherein the plantlet is further cultured on a rooting medium until a root system is developed thereon.

6. The method of claim 5 wherein said plantlet having a root system is transferred to a medium comprising soil and allowed to grow thereon until a whole plant is generated therefrom.

7. The method of claim 1 in which an embryo of step (b) is further cultured to regenerate a whole plant.

8. The method of claim 1 wherein the induction medium comprises a sugar selected from the group consisting of sucrose, glucose, and maltose and mixtures thereof.

9. The method of claim 1 wherein said cotyledon tissue is transformed by the incorporation of foreign DNA into the genome thereof prior to the generation of somatic embryos.

10. A method of producing a plant of *Glycine max* containing foreign DNA comprising:
   a) macerating cotyledon tissue taken from immature embryos of said species comprising the "fertile crescent" region by crushing on mesh;
   (b) contacting said macerated tissue with said foreign DNA such that said DNA is incorporated into the cells of said tissue;
   c) contacting said macerated tissue of step (b) with an embryogenic medium, which embryogenic medium comprises an auxin of the NAA family at a concentration between about 5 mg/l and about 50 mg/l, for said tissue to produce somatic embryos;

d) transferring said embryos to suitable media for regeneration of whole plants containing foreign DNA therefrom.

11. The method of claim 10 wherein Agrobacteria are used as vectors for transferring said foreign DNA to said macerated tissue in step (b).

12. The method of claim 10 wherein following step (b) said tissue is grown on a selection medium which prevents or inhibits the growth of untransformed tissue.

13. The method of claim 10 wherein following step (b) no selection medium which prevents or inhibits the growth of untransformed tissue is used, and transformants are identified and selected through the identification of a phenotype conferred by said foreign DNA.

14. In a process for regenerating plants of *Glycine max* by culturing somatic tissue of *Glycine max* on a nutrient medium containing an auxin so as to form somatic embryos, and placing said embryos on suitable media for regeneration of whole plants, the improvement comprising culturing fertile regions selected from the group consisting of the "fertile crescent" or "fertile oval" regions of immature cotyledonary tissue.

15. The process of claim 14 in which said fertile regions of tissue are macerated prior to placement on the nutrient medium.

16. The process of claim 14 in which said fertile regions consist essentially of the "fertile crescent" region.

17. The process of claim 14 in which said fertile regions of tissue are transformed by contacting with foreign DNA prior to regeneration.

18. A method for generating a whole plant from cotyledonary tissue of immature embryos or cotyledons therefrom of a plant of *Glycine max* comprising culturing cells of said tissue on a medium containing less than about 2% (w/v) carbohydrate comprising a sugar selected from the group consisting of glucose, sucrose and maltose, and mixtures thereof, and an auxin selected from the group consisting of 2,4-D and NAA at a concentration between about 5.0 mg/l and about 50 mg/l to generate an embryo and placing said embryo on appropriate media whereby a whole plant is regenerated.

19. The method of claim 18 wherein said medium contains about 10 mg/l auxin.

20. The method of claim 19 wherein said auxin comprises NAA.

21. The method of claim 19 wherein said carbohydrate is present in a concentration of about 1.5%.

22. The method of claim 18 wherein said carbohydrate comprises a sugar selected from the group consisting of glucose and sucrose, and mixtures thereof.

23. The method of claim 18 wherein said auxin is 2,4-D.

24. The method of claim 18 wherein said auxin is NAA.

25. The method of claim 18 wherein said cotyledon tissue has been wounded or has had any embryonic aces excised therefrom.

26. The method of claim 18 wherein said cells are taken from the fertile crescent region of said cotyledon tissue.

27. The method of claim 18 wherein said cotyledon tissue is macerated by pressing against a mesh so as to separate said tissue into visible groups of cells.

28. The method of claim 18 wherein said cells have been transformed by the insertion of foreign DNA into the genome thereof.

29. The method of claim 27 wherein said cells have been transformed by the insertion of foreign DNA into the genome thereof.

30. A process for transferring *Glycine max* tissue with foreign DNA and regenerating whole transformed *Glycine max* plants therefrom which comprises the steps of:

macerating selected embryogenic portions of cotyledonary tissue of immature embryos of *Glycine max* with a mesh;

contacting said macerated tissue with said foreign DNA followed by growing said macerated tissue on media not containing a selection agent; and either identifying transformants of said tissue growing on said media solely by means of a phenotypic trait conferred by said foreign DNA to cells of said tissue and regenerating whole transformed plants from said transformants, or regenerating plants from said tissue and identifying transformants of said plants solely by means of a phenotypic trait conferred by said foreign DNA to said regenerated plants, thereby producing whole *Glycine max* plants transformed with said foreign DNA.

31. The process of claim 30 wherein said tissue is macerated such that it comprises small, visible pieces about ¼ mm² or less in size.

* * * * *

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

It is certified that error appears in the above-identified patent and that said Letters Patent is hereby corrected as shown below:

On the title page, item [56] Reference Cited rewrite "Ranch et al., 1985 In Vitro," as --Ranch et al., In Vitro Cell. & Dev. Biol.,--.

Column 1, line 68, rewrite "G. max" as -- $\underline{G.\ max}$ --.

Column 2, line 21, rewrite "Lett" as --Lett.--.

Column 2, line 30, rewrite "GlYcine" as --$\underline{Glycine}$--.

Column 2, line 31, rewrite "Lett., Vol. 21" as --Lett. Vol. 21--.

Column 2, line 68, insert --,-- between "Iowa" and "August".

Column 3, line 44, rewrite "disclose or claim" as --discloses and claims--.

Column 3, line 64, rewrite "00.25 as --0.25--.

Column 4, line 10, "2,4" should not be in bold-face type.

Column 4, line 15, rewrite "$\underline{max}$"," as --$\underline{max}$,"--.

UNITED STATES PATENT AND TRADEMARK OFFICE
CERTIFICATE OF CORRECTION

PATENT NO. : 5,024,944
DATED : Jun. 18, 1991
INVENTOR(S) : Glenn B. Collins, et al It is certified that error appears in the above-identified patent and that said Letters Patent is hereby corrected as shown below:

Column 4, lines 16-17, align line 16 with line 17 to omit extraneous spacing.

Column 4, line 26, "2,4" should not be in bold-face type.

Column 4, line 35, rewrite "G. max" as --G. max--.

Column 4, line 36, "2,4" should not be in bold-face type.

Column 4, line 55, rewrite "Soybeans," as --Soybeans,"--.

Column 4, line 57, insert --,-- between "658" and "describe".

Column 5, line 1, rewrite "(1985)" as --(1985),--.

Column 5, line 2, rewrite "canescens," as --canescens,"--.

Column 5, line 3, insert --,-- between "149" and "describe".

Column 5, line 31, rewrite "L. Merr.), "Plant" as --L. Merr.)," Plant--.

Column 5, line 31, insert --,-- after "143".

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

Page 3 of 9

It is certified that error appears in the above-identified patent and that said Letters Patent is hereby corrected as shown below:

Column 5, line 35, "2,4" should not be in bold-face type.

Column 5, line 38, rewrite "reported," as --reported;--.

Column 5, line 50, insert --,-- between "Hood" and "et al.", and also after "(1984)".

Column 5, line 53, rewrite "Plants"," as --Plants,"--.

Column 5, line 57, rewrite "Plants," as --Plant,"--.

Column 5, line 63, "tumefacien," should read --*tumefacien*,"--.

Column 6, line 4, insert --,-- between "Wyndale" and "et al.".

Column 6, line 7, rewrite "deseribed" as --describe--.

Column 6, line 10, insert --,-- between "Owens" and "et al.".

Column 6, line 17, rewrite "cGMP"," as --cGMP,"--.

Column 6, line 24, rewrite "discloses" as --disclose--.

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

It is certified that error appears in the above-identified patent and that said Letters Patent is hereby corrected as shown below:

Column 6, line 27, insert --,-- between "Simpson" and "et al.".

Column 6, line 30, rewrite "discloses" as --disclose--.

Column 6, line 38, rewrite "Rhizogene" summarizes" as --Rhizogene," summarize--.

Column 6, line 39, "states" should read --state--

Column 6, line 45, rewrite "(1985) "Genotypic" as --(1985), "Genotypic--.

Column 6, line 58, rewrite "describes" as --describe--.

Column 6, line 65, insert --,-- between "Byrne" and "et al.".

Column 6, line 67, rewrite "discusses" as -- discuss--.

Column 7, line 2, rewrite "describes" as --describe--.

Column 7, line 23, rewrite "refers" as --ranges--.

Column 7, line 46, rewrite "medium, embryo" as --medium," "embyo--.

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

It is certified that error appears in the above-identified patent and that said Letters Patent is hereby corrected as shown below:

Column 9, line 26, rewrite "northern" as --Northern--.

Column 9, line 27, rewrite "western" as --Western--.

Column 13, line 53, rewrite "phytogar Phytoagar" as --Phytogar--.

Column 14, line 17, rewrite "34-57" as --34-157--.

Column 15, line 48, insert --gellan-- between "Gelrite" and "gum".

Column 15, line 48, insert --,-- after "agent".

Column 15, line 55, rewrite "possibly" as --possible--.

Column 17, line 8, rewrite "3211" as --3213--.

Column 17, line 60, rewrite "Cell," as --Cell--.

Column 18, line 17, rewrite ""normal," as --"normal,"--.

Column 18, line 19, rewrite ""abnormal Bipolar" as --"abnormal." Bipolar--.

Column 20, line 59, rewrite ""germinated"" as --"germinated."--.

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

It is certified that error appears in the above-identified patent and that said Letters Patent is hereby corrected as shown below:

Column 23, line 15, insert --"inductive" auxin-- between "for" and "concentrations".

Column 30, line 5, rewrite "recallussed" as --recallused--.

Column 30, line 53, rewrite "615.)" as --615)--.

Column 33, line 19, rewrite "Were" as --were--.

Column 36, line 2, delete "boxes".

Column 36, line 12, rewrite "White¹" as --White--.

Column 38, line 4, rewrite "mix:sand sand mix" as --mix:sand mix--.

Column 39, line 21, rewrite "mix:sand sand mix" as --mix:sand mix--.

Column 39, line 22, rewrite "20:20 20" as --20:20:20--.

Column 45, line 41, insert --Gelrite-- between "0.2%" and "gellan".

UNITED STATES PATENT AND TRADEMARK OFFICE
CERTIFICATE OF CORRECTION

PATENT NO. : 5,024,944

DATED : Jun. 18, 1991

INVENTOR(S) : Glenn B. Collins, et al

It is certified that error appears in the above-identified patent and that said Letters Patent is hereby corrected as shown below:

Column 45, line 49, rewrite "1 mg/l" as --10 mg/l--.

Column 45, line 53, insert --,-- between "mg/l" and "α".

Column 46, Table 20, first column under "GENOTYPE Time of inoculation", first line of table, rewrite "0 days" as --0 day--.

Column 46, line 54, insert --Gelrite-- between "and" and "gellan".

Column 46, line 63, insert --Gelrite-- between "+" and "gellan".

Column 46, line 67, insert --Gelrite-- between "+" and "gellan".

Column 47, line 3, insert --Gelrite-- between "+" and "gellan".

Column 47, line 7, insert --Gelrite-- between "+" and "gellan".

UNITED STATES PATENT AND TRADEMARK OFFICE
CERTIFICATE OF CORRECTION

PATENT NO. : 5,024,944
DATED : June 18, 1991
INVENTOR(S) : GLENN B. COLLINS, ET AL It is certified that error appears in the above-indentified patent and that said Letters Patent is hereby corrected as shown below:

Column 47, line 11, insert --Gelrite-- between "+" and "gellan".

Column 47, line 15, insert --*-- before "G15", and insert --Gelrite-- between "+" and "gellan".

Column 47, line 19, insert --Gelrite-- between "+" and "gellan".

Column 47, line 23, insert --Gelrite-- between "+" and "gellan".

UNITED STATES PATENT AND TRADEMARK OFFICE
CERTIFICATE OF CORRECTION

PATENT NO. : 5,024,944
DATED : June 18, 1991
INVENTOR(S) : Glenn B. COLLINS, ET AL It is certified that error appears in the above-indentified patent and that said Letters Patent is hereby corrected as shown below:

Column 47, line .29, insert "Gelrite" between "on" and "gellan".

Column 47, line 29, rewrite "G10or" as --G10 or--.

Column 50, line 11, (claim 25), "aces" should read --axes--.

Column 50, line 25, (Claim 30), rewrite "transferring" as --transforming--.

Signed and Sealed this

Fourteenth Day of June, 1994

Attest:

BRUCE LEHMAN

Attesting Officer

Commissioner of Patents and Trademarks